United States Patent
Dhanak et al.

(10) Patent No.: US 6,713,502 B2
(45) Date of Patent: Mar. 30, 2004

(54) ANTI-INFECTIVES

(75) Inventors: Dashyant Dhanak, King of Prussia, PA (US); Thomas Carr, Collegeville, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/275,426

(22) PCT Filed: May 4, 2001

(86) PCT No.: PCT/US01/14525

§ 371 (c)(1),
(2), (4) Date: Nov. 5, 2002

(87) PCT Pub. No.: WO01/85720

PCT Pub. Date: Nov. 15, 2001

(65) Prior Publication Data

US 2004/0010030 A1 Jan. 15, 2004

Related U.S. Application Data

(60) Provisional application No. 60/201,945, filed on May 5, 2000.

(51) Int. Cl.[7] .............. A61K 31/40; C07D 409/00; C07D 207/00

(52) U.S. Cl. .............. 514/422; 514/423; 548/527; 548/533

(58) Field of Search .............. 514/422, 423; 548/527, 533

(56) References Cited

U.S. PATENT DOCUMENTS 6,239,150 B1    5/2001   Oshima et al.

FOREIGN PATENT DOCUMENTS

WO    WO 00/09543    2/2000

OTHER PUBLICATIONS

Han, et al., "Alpha–Ketomides, Alpha–Ketoesters and Alpha–Diketones as HCV NS3 Protease Inhibitors". *Bioorganic & Medicinal Chemistry Letters*, 10(8): 711–713 (2000).

*Primary Examiner*—Deborah C. Lambkin
(74) *Attorney, Agent, or Firm*—Kathryn L. Sieburth; Mary E. McCarthy; Charles M. Kinzig

(57) ABSTRACT

Novel anti-infective and methods of using them are provided.

8 Claims, No Drawings

ANTI-INFECTIVES

This application claims the benefit of provisional application 60/201,945 filed May 5, 2000.

FIELD OF THE INVENTION

The present invention relates to novel anti-infectives. Specifically, the present invention involves novel HCV inhibitors.

BACKGROUND OF THE INVENTION

First identified by molecular cloning in 1989 (Choo et al., 1989), hepatitis C virus (HCV) is now widely accepted as the most common causative agent of post-transfusion non A, non-B hepatitis (NANBH) (Kuo et al., 1989). Due to its genome structure and sequence homology, this virus was assigned as a new genus in the Flaviviridae family, along with the other two genera, flaviviruses (such as yellow fever virus and Dengue virus types 1–4) and pestiviruses (such as bovine viral diarrhea virus, border disease virus, and classic swine fever virus) (Choo et al., 1989; Miller and Purcell, 1990). Like the other members of the Flaviviridae, HCV is an enveloped virus containing a single strand RNA molecule of positive polarity. The HCV genome is approximately 9.6 kilobases (kb) with a long, highly conserved, noncapped 5'nontranslated region (NTR) of approximately 340 bases which functions as an internal ribosome entry site (IRES) (Wang and Siddiqui, 1995). This element is followed by a region which encodes a single long open reading frame (ORF) encoding a polypeptide of ~3000 amino acids comprising both the structural and nonstructural viral proteins. Upon entry into the cytoplasm of the cell, this RNA is directly translated into a polypeptide of ~3000 amino acids comprising both the structural and nonstructural viral proteins. This large polypeptide is subsequently processed into the individual structural and nonstructural proteins by a combination of host and virally-encoded proteinases (reviewed in Rice, 1996). Following the termination codon at the end of the long ORF, there is a 3'NTR which roughly consists of three regions: an ~40 base region which is poorly conserved among various genotypes, a variable length poly (U)/polypyrimidine tract, and a highly conserved 98 base element also called the "3'Xtail" (Kolykhalov et al., 1996; Tanaka et al., 1995; Tanaka et al., 1996; Yamada et al., 1996). The 3'NTR is predicted to form a stable secondary structure which is essential for HCV growth in chimps and is believed to function in the initiation and regulation of viral RNA replication.

Infection with HCV is a major cause of human liver disease throughout the world with seroprevalence in the general population ranging from 0.3 to 2.2% (van der Poel et al., 1994) to as high as ~10–20% in Egypt (Hibbs et al., 1993). HCV is most commonly transmitted via blood (Alter et al., 1993). Of these initial infections, an estimated 30% are symptomatic. However, more than 85% of all infected individuals become chronically infected (3.9 million current chronic infections in US, 170 million chronic infections worldwide, estimated 33,200 new cases in 1994 in US). Chronic HCV infection accounts for 30% of all cirrhosis, end-stage liver disease, and liver cancer in the U.S. Of the total chronic cases in the US, greater than 118,000 will go on to develop hepatocellular carcinoma (HCC) (which represents ≧25% of all liver cancers) as a direct result of HCV infection (reviewed in Hoofnagle, 1997; Seeff, 1997). There are 8,000–12,000 deaths per year in the US currently attributed to HCV infection, and treatment costs were estimated at 600 million for 1992 in the US. The CDC estimates that the number of deaths due to HCV will increase to 38,000/yr. by the year 2010.

Due to the high degree of variability in the viral surface antigens, existence of multiple viral genotypes, and demonstrated specificity of immunity, the development of a successful vaccine in the near future is unlikely. Although initially therapy consisted of interferon alone, combination therapy of interferon alpha-2b (□-IFN, 3 million units injected subcutaneously three times weekly) with ribavirin (1–1.2 gms twice daily orally) for either 24 or 48 weeks is currently the most efficacious approved therapy for the treatment of chronic HCV infection. Schering-Plough alone reported over $430 million in sales for interferon alone in 1998 specifically for HCV therapy. The response and sustained response rates for combination therapy were better than interferon alone (80% initial response for combo vs. 46% for IFN alone; and 30–50% sustained response for combo vs. 5–13% for IFN alone). However, there were still many adverse side effects associated with combination therapy (flu-like symptoms, leukopenia, thrombocytopenia, depression, etc. from interferon), as well as anemia induced by ribavirin (reviewed in Lindsay, 1997). Furthermore, this therapy was still less effective against infections caused by HCV genotype 1 which constitutes ~75% of all HCV infections in the developed markets (as opposed to other HCV genotypes). Analogous to therapy for HIV infection, combination therapy (i.e. IFN plus antiviral or antiviral cocktail) is likely to be the most efficacious therapy.

In the US, an estimated 3.9 million Americans are infected with HCV. Although only 30% of acute infections are symptomatic, >85% of infected individuals develop chronic, persistent infection. There are 8,000–10,000 deaths per year in the US currently attributed to HCV infection, and treatment costs are estimated at >600 million/yr. (1992 CDC estimate for US). Worldwide over 170 million people are estimated to be infected chronically. HCV infection is responsible for 40–60% of all chronic liver disease and 30% of all liver transplants. A vaccine is unlikely due to hypervariable surface antigens and demonstrated specificity of immunity.

Currently, there are no HCV antiviral agents available, with alpha-interferon (alone or in combination with ribavirin) being the only approved treatment. Many adverse side effects are associated with therapy (flu-like symptoms, leukopenia, thrombocytopenia, depression, anemia, etc.); only ~50–80% of the patients respond (reduction in serum HCV RNA levels, normalization of liver enzymes); however, of those treated, 50–70% relapse within 6 months of cessation of therapy.

The NS5B protein (591 amino acids, 65 kDa) of HCV (Behrens et al., 1996), encodes an RNA-dependent RNA polymerase (RdRp) activity and contains canonical motifs present in other RNA viral polymerases. The NS5B protein is fairly well conserved both intratypically (one type 1b isolate vs. another type 1b isolate, ~95–98% aa identity) and intertypically (type 1a vs. type 1b, ~85% aa identity). The essentiality of the HCV NS5B RdRp activity for the generation of infectious progeny virions has been formally proven in chimpanzees (A. A. Kolykhalov et al..abstract, 1999) and inhibition of NS5B RdRp activity is therefore predicted to be antiviral for HCV infection, and inhibition of RNA replication would be expected to cure infection.

Based on the foregoing, there exists a significant need to identify synthetic or biological compounds for their ability to inhibit HCV.

SUMMARY OF THE INVENTION

The present invention involves compounds represented hereinbelow, pharmaceutical compositions comprising such compounds and methods of using the present compounds.

DETAILED DESCRIPTION OF THE INVENTION

The compounds useful in the present methods are selected from Formula (I) hereinbelow:

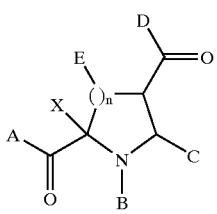

wherein:
A represents $OR_1$, $NR1R_2$, or $R_1$ wherein $R_1$ and $R_2$ is selected from the group consisting of hydrogen, $C_{1-6}$alkyl, optionally substituted aryl, alkylaryl, arylalkyl;
B represents hydrogen, $C(O)R_1$ wherein $R_1$ is selected from the group consisting of hydrogen, $C_{1-6}$alkyl, aryl, alkylaryl, arylalkyl;
C represents hydrogen, $C_{1-6}$alkyl, or optionally substituted aryl;
D represents $OR_1$, $NR_1R_2$, or $R_1$ wherein $R_1$ and $R_2$ is selected from the group consisting of hydrogen, $C_{1-6}$alkyl, aryl, alkylaryl, arylalkyl;
E represents hydrogen, $C_{1-6}$alkyl, optionally substituted aryl, alkylaryl, arylalkyl;
X represents $C_{1-6}$alkyl, optionally substituted aryl, alkylaryl, arylalkyl;
n is 1 or 2 or 3.
Preferably, A is selected from the group consisting of OH, $OR_1$;
Preferably, B is selected from the group consisting of $C(O)R_1$;
Preferably, C is selected from the group consisting of optionally substituted aryl;
Preferably, D is selected from the group consisting of OH, $OR_1$;
Preferably, E is hydrogen;
Preferably, X is selected from the group consisting of $C_{1-6}$alkyl, alkylaryl
Preferably n is 1 or 2.

As used herein, "alkyl" refers to an optionally substituted hydrocarbon group joined together by single carbon-carbon bonds. The alkyl hydrocarbon group may be linear, branched or cyclic, saturated or unsaturated. Preferably, the group is linear. Preferably, the group is unsubstituted. Preferably, the group is saturated. Preferred alkyl moieties are $C_{1-4}$ alkyl, most preferably methyl.

As used herein, "aryl" refers to an optionally substituted aromatic group with at least one ring having a conjugated pi-electron system, containing up to two conjugated or fused ring systems. "Aryl" includes carbocyclic aryl, heterocyclic aryl and biaryl groups, all of which may be optionally substituted. Preferred aryl moieties are phenyl, unsubstituted, monosubstituted, disubstituted or trisubstituted. Preferred heteroaryl moieties are selected from the group consisting of unsubstituted, monosubstituted, disubstituted or trisubstituted thienyl, quinolinyl, indolyl and pyridinyl. Preferred aryl and heteroaryl substituents are selected from the group consisting of $C_{1-4}$ alkyl, $N(C_{1-4}$ alkyl$)_2$, halo, $OC_1$–$C_4$ alkyl, CH═CH, $CF_3$, pyridine, phenyl, $NO_2$, OH and MeO.

More preferably, alkyl substituents are methyl or ethyl. More preferably, halo substituents are chloro or bromo.

Preferred compounds useful in the present invention are selected from the group consisting of:
2-Isobutyl-5-thiophene-2-yl-1-[1-(4-trifluoromethyl-phenyl)-methanoyl]-pyrrolidine-2,4-dicarboxylic acid 4-methyl ester
5-(3-Fluoro-phenyl)-2-isobutyl-1-[1-(4-trifluoromethyl-phenyl)-methanoyl]-pyrrolidine-2,4-dicarboxyl acid 4-methyl ester
1-[1-(3,4-Dichloro-phenyl)-methanoyl]-5-(3-fluoro-phenyl)-2-isobutyl-pyrrolidine-2,4-dicarboxylic acid 4-methyl ester
2-Isobutyl-5-(3-methoxy-phenyl)-1-[1-(4-trifluoromethyl-phenyl)-methanoyl]-pyrrolidine-2,4-dicarboxylic acid 4-methyl ester
1-[1-(3,4-Dichloro-phenyl)-methanoyl]-2-isobutyl-5-(3-methoxy-phenyl)-pyrrolidine-2,4-dicarboxylic acid 4-methyl ester
5-(2-Chloro-5-trifluoromethyl-phenyl)-2-isobutyl-1-[1-(4-trifluoromethyl-phenyl)-methanoyl]-pyrrolidine-2,4-dicarboxylic acid 4-methyl ester
5-(2-Chloro-5-trifluoromethyl-phenyl)-1-[1-(3,4-dichloro-phenyl)-methanoyl]-2-isobutylpyrrolidine-2,4-dicarboxylic acid 4-methyl ester
2-Benzyl-5-(2-chloro-5-trifluoromethyl-phenyl)-1-[1-(4-trifluoromethyl-phenyl)-methanoyl]-pyrrolidine-2,4-dicarboxylic acid 4-methyl ester
2-Benzyl-5-thiophen-2-yl-1-[1-(4-trifluoromethyl-phenyl)-methanoyl]-pyrrolidine-2,4-dicarboxylic acid 4-methyl ester
2-Benzyl-1-[1-(3,4-dichloro-phenyl)-methanoyl]-5-thiophen-2-yl-pyrrolidine-2,4-dicarboxylic acid 4-methyl ester
2-Benzyl-5-(3-fluoro-phenyl)-1-[1-(4-trifluoromethyl-phenyl)-methanoyl]-pyrrolidine-2,4-dicarboxylic acid 4-methyl ester
2-Benzyl-1-[1-(3,4-dichloro-phenyl)-methanoyl]-5-(3-fluoro-phenyl)-pyrrolidine-2,4-dicarboxylic acid 4-methyl ester
2-Benzyl-5-(3-methoxy-phenyl)-1-[1-(4-trifluoromethyl-phenyl)-methanoyl]-pyrrolidine-2,4-dicarboxylic acid 4-methyl ester
5-(3-Bromo-4,5-dimethoxy-phenyl)-2-methyl-1-[1-(4-trifluoromethyl-phenyl)-methanoyl]-pyrrolidine-2,4-dicarboxylic acid 4-methyl ester
2-Isobutyl-5-thiophene-2-yl-1-[1-(4-trifluoromethyl-phenyl)-methanoyl]-pyrrolidine-2,4-dicarboxylic acid
1-[1-(3,4-Dichloro-phenyl)-methanoyl]-5-(3-fluoro-phenyl)-2-isobutyl-pyrrolidine-2,4-dicarboxylic acid
1-[1-(3,4-Dichloro-phenyl)-methanoyl]-2-isobutyl-5-(3-methoxy-phenyl)-pyrrolidine-2,4-dicarboxylic acid
5-(2-Chloro-5-trifluoromethyl-phenyl)-1-[1-(3,4-dichloro-phenyl)-methanoyl]-2-isobutyl-pyrrolidine-2,4-dicarboxylic acid
5-(2-Chloro-5-trifluoromethyl-phenyl)-2-isobutyl-1-[1-(4-trifluoromethyl-phenyl)-methanoyl]-pyrrolidine-2,4-dicarboxylic acid
1-[1-(3,4-Dichloro-phenyl)-methanoyl]-2-isobutyl-5-(2,3,5-trichloro-phenyl)-pyrrolidine-2,4-dicarboxylic acid
5-(3-Bromo-4,5-dimethoxy-phenyl)-2-methyl-1-[1-(4-trifluoromethyl-phenyl)-methanoyl]-pyrrolidine-2,4-dicarboxylic acid 2-Benzyl-5-thiophen-2-yl-1-[1-(4-trifluoromethyl-phenyl)-methanoyl]-pyrrolidine-2,4-dicarboxylic acid 2-Benzyl-1-[1-(3,4-dichloro-phenyl)-methanoyl]-5-(3-fluoro-phenyl)-pyrrolidine-2,4-dicarboxylic acid 2-Benzyl-5-(3-fluoro-phenyl)-1-[1-(4-trifluoromethyl-phenyl)-methanoyl]-pyrrolidine-2,4-dicarboxylic acid 2-Benzyl-5-(3-methoxy-phenyl)-1-[1-(4-trifluoromethyl-phenyl)-methanoyl]-pyrrolidine-2,4-dicarboxylic acid 2-Benzyl-5-(2-chloro-5-trifluoromethyl-phenyl)-1-[1-(4-trifluoromethyl-phenyl)-methanoyl]-pyrrolidine-2,4-dicarboxylic acid 2-Benzyl-1-[1-(3,4-dichloro-phenyl)-methanoyl]-5-(2,3,5-trichloro-phenyl)-pyrrolidine-2,4-dicarboxylic acid Also included in the present invention are pharmaceutically acceptable salt complexes. Preferred are the ethylene diamine, sodium, potassium, calcium, ethanolamine, hydrochloride, hydrobromide and trifluoroacetate salts. The compounds of the present invention may contain one or more asymmetric carbon atoms and may exist in racemic and optically active forms. All of these compounds and diastereomers are contemplated to be within the scope of the present invention.

Also included in the present invention is a process according to Scheme 1 for the synthesis of the compounds using a suitable solid phase such as Wang, Merrifield, BAL or other suitable resin.

Wang bound Fmoc-L-leucine (5.0 gm, 0.6 mmol/gm loading) was suspended in a 20% piperidine/dimethylformamide solution (10 mL) and shaken for 20 minutes. The solution was decanted from the resin and the resin treated again with a second fresh solution (10 mL) for 30 minutes. The resin was filtered and washed successively with dimethylformamide x3, dichloromethane x4, methanol x4, and dichloromethane x3. A portion of the resin (0.5 gm, 0.3 mmol) was suspended in toluene (7 mL) and treated with thiophene-2-carboxaldehyde (10 eq., 0.3 mL). The mixture was heated to 80C and shaken for 16 hours on an orbital sand bath. The mixture was allowed to cool and filtered. The resin was washed with toluene x5.

b) Wang resin bound 2-Isobutyl-5-thiophen-2-yl-pyrrolidine-2,4-dicarboxylic acid 4-methyl ester The compound of Example 1(a) (0.5 gm, 0.3 mmol) was suspended in toluene (7 mL) and acetic acid (0.5 mL). The mixture was treated with methyl acrylate (10 eq., 0.14 mL). The mixture was heated to 80C and shaken for 12 hours on an orbital sand bath. The resin was filtered and washed successively with toluene x4, dichloromethane x3, methanol x3, and dichloromethane x3.

c) Wang resin bound 2-Isobutyl-5-thiophen-2-yl-1-[1-(4-trifluoromethyl-phenyl)-methanoyl]pyrrolidine-2,4-dicarboxylic acid 4-methyl ester The compound of Example 1(b) (0.5 gm, 0.3 mmol) was suspended in pyridine (8 mL) and treated with

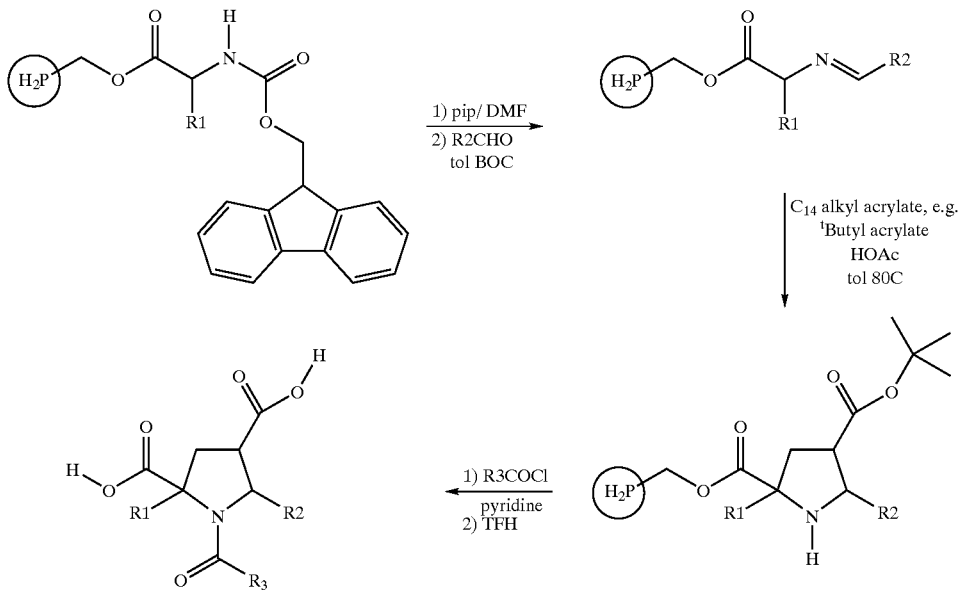

Scheme 1

With appropriate manipulation and protection of any chemical functionality, synthesis of the remaining compounds of Formula (I) is accomplished by methods analogous to those above and to those described in the Experimental section.

EXAMPLE 1

Preparation of 2-isobutyl-5-thiophene-2-yl-1-[1-(4-trifluoromethyl-phenyl)-methanoyl]-pyrrolidine-2,4-dicarboxylic acid 4-methyl ester a) Wang resin bound -4-methyl-2-[(thiophen-2-ylmethylene)-amino]-pentanoic acid 4-trifluoromethyl benzoyl chloride (10 eq., 0.5 mL). The mixture was shaken at room temperature for 14 hours. The resin was filtered and washed successively with dichloromethane x3, methanol x4, and dichloromethane x3.

d) 2-Isobutyl-5-thiophen-2-yl-1-[1-(4-trifluoromethyl-phenyl)-methanoyl]-pyrrolidine-2,4-dicarboxylic acid 4-methyl ester The compound of Example 1(c) was treated with neat trifluoroacetic acid for 10 hours. The solution was removed from the resin and the resin washed with dichloromethane x3. The TFA solution and washes were combined and evaporated. The residue was chromatographed using Gilson reverse phase HPLC to give the desired compound as a tan solid (21.2 mg). MS [M+H]$^{+}$+484.4

EXAMPLE 2

Preparation of 5-(3-Fluoro-phenyl)-2-isobutyl-1-[1-(4-trifluoromethyl-phenyl)-methanoyl]-pyrrolidine-2,4-dicarboxyl acid 4-methyl ester Following the procedure of Example 1(a)–1(d), except substituting 3-fluorobenzaldehyde for thiophene-2-carboxaldehyde, the title compound was prepared as a solid. MS [M+H]+ 496.4

EXAMPLE 3

Preparation of 1-[1-(3,4-Dichloro-phenyl)-methanoyl]-5-(3-fluoro-phenyl)-2-isobutyl-pyrrolidine-2,4-dicarboxylic acid 4-methyl ester Following the procedure of Example 1(a)–1(d), except substituting 3-fluorobenzaldehyde for thiophene-2-carboxaldehyde and substituting 3,4 dichlorobenzoyl chloride for 4-trifluoromethyl benzoyl chloride, the title compound was prepared as a solid. MS [M+H]+496.4

EXAMPLE 4

Preparation of 2-Isobutyl-5-(3-methoxy-phenyl)-1-[1-(4-trifluoromethyl-phenyl)-methanoyl]-pyrrolidine-2,4-dicarboxylic acid 4-methyl ester Following the procedure of Example 1(a)–1(d), except substituting m-anisaldehyde for thiophene-2-carboxaldehyde, the title compound was prepared as a solid. MS [M+H]+508.4

EXAMPLE 5

Preparation of 1-[1-(3,4-Dichloro-phenyl)-methanoyl]-2-isobutyl-5-(3-methoxy-phenyl)-pyrrolidine-2,4-dicarboxylic acid 4-methyl ester Following the procedure of Example 1(a)–1(d), except substituting m-anisaldehyde for thiophene-2-carboxaldehyde and substituting 3,4 dichlorobenzoyl chloride for 4-trifluoromethyl benzoyl chloride, the title compound was prepared as a solid. MS [M+H]+508.2

EXAMPLE 6

Preparation of 5-(2-Chloro-5-trifluoromethyl-phenyl)-2-isobutyl-1-[1-(4-trifluoromethyl-phenyl)-methanoyl]-pyrrolidine-2,4-dicarboxylic acid 4-methyl ester Following the procedure of Example 1(a)–1(d), except substituting 2-chloro-5-trifluoromethyl benzaldehyde for thiophene-2-carboxaldehyde, the title compound was prepared as a solid. MS [M+H]+580.4

EXAMPLE 7

Preparation of 5-(2-Chloro-5-trifluoromethyl-phenyl)-1-[1-3,4-dichloro-phenyl)-methanoyl]-2-isobutyl-pyrrolidine-2,4-dicarboxylic acid 4-methyl ester Following the procedure of Example 1(a)–1(d), except substituting 2-chloro-5-trifluoromethyl benzaldehyde for thiophene-2-carboxaldehyde and substituting 3,4 dichlorobenzoyl chloride for 4-trifluoromethyl benzoyl chloride, the title compound was prepared as a solid. MS [M+H]+ 580.4

EXAMPLE 8

Preparation of 2-Benzyl-5-(2-chloro-5-trifluoromethyl-phenyl)-1-[1-(4-trifluoromethyl-phenyl)-methanoyl]-pyrrolidine-2,4-dicarboxylic acid 4-methyl ester Following the procedure of Example 1(a)–1(d), except beginning with Wang bound Fmoc-L-phenylalanine instead of Wang bound Fmoc-L-leucine and substituting 2-chloro-5-trifluoromethyl benzaldehyde for thiophene-2-carboxaldehyde, the title compound was prepared as a solid. MS [M+H]+614.4

EXAMPLE 9

Preparation of 2-Benzyl-5-thiophen-2-yl-1-[1-(4-trifluoromethyl-phenyl)-methanoyl]-pyrrolidine-2,4-dicarboxylic acid 4-methyl ester Following the procedure of Example 1(a)–1(d), except beginning with Wang bound Fmoc-L-phenylalanine instead of Wang bound Fmoc-L-leucine, the title compound was prepared as a solid. MS [M+H]+518.4

EXAMPLE 10

Preparation of 2-Benzyl-1-[1-(3,4-dichloro-phenyl)-methanoyl]-5-thiophen-2-yl-pyrrolidine-2,4-dicarboxylic acid 4-methyl ester Following the procedure of Example 1(a)–1(d), except beginning with Wang bound Fmoc-L-phenylalanine instead of Wang bound Fmoc-L-leucine and substituting 3,4 dichlorobenzoyl chloride for 4-trifluoromethyl benzoyl chloride, the title compound was prepared as a solid. MS [M+H]+ 518.4

EXAMPLE 11

Preparation of 2-Benzyl-5-(3-fluoro-phenyl)-1-[1-(4-trifluoromethyl-phenyl)-methanoyl]-pyrrolidine-2,4-dicarboxylic acid 4-methyl ester Following the procedure of Example 1(a)–1(d), except beginning with Wang bound Fmoc-L-phenylalanine instead of Wang bound Fmoc-L-leucine and substituting 3-fluorobenzaldehyde for thiophene-2-carboxaldehyde, the title compound was prepared as a solid. MS [M+H]+530.4

EXAMPLE 12

Preparation of 2-Benzyl-1-[1-(3,4-dichloro-phenyl)-methanoyl]-5-(3-fluoro-phenyl)-pyrrolidine-2,4-dicarboxylic acid 4-methyl ester Following the procedure of Example 1(a)–1(d), except beginning with Wang bound Fmoc-L-phenylalanine instead of Wang bound Fmoc-L-leucine and substituting 3-fluorobenzaldehyde for thiophene-2-carboxaldehyde and 3,4 dichlorobenzoyl chloride for 4-trifluoromethyl benzoyl chloride, the title compound was prepared as a solid. MS [M+H]+530.2

EXAMPLE 13

Preparation of 2-Benzyl-5-(3-methoxy-phenyl)-1-[1-(4-trifluoromethyl-phenyl)-methanoyl]-pyrrolidine-2,4-dicarboxylic acid 4-methyl ester Following the procedure of Example 1(a)–1(d), except beginning with Wang bound Fmoc-L-phenylalanine instead of Wang bound Fmoc-L-leucine and substituting m-anisaldehyde for thiophene-2-carboxaldehyde, the title compound was prepared as a solid. MS [M+H]$^+$542.4

EXAMPLE 14

Preparation of 5-(3-Bromo-4,5-dimethoxy-phenyl)-2-methyl-1-[1-(4-trifluoromethyl-phenyl)-methanoyl]-pyrrolidine-2,4-dicarboxylic acid 4-methyl ester Following the procedure of Example 1(a)–1(d), except beginning with Wang bound Fmoc-L-alanine instead of Wang bound Fmoc-L-leucine and substituting 3-bromoveratraldehyde for thiophene-2-carboxaldehyde, the title compound was prepared as a solid. MS [M+H]$^+$ 574.4

EXAMPLE 15

Preparation of 2-isobutyl-5-thiophene-2-yl-1-[1-(4-trifluoromethyl-phenyl)-methanoyl]-pyrrolidine-2,4-dicarboxylic acid Following the procedure of Example 1(a)–1(d), except substituting tert-butyl acrylate (0.5 mL) for methyl acrylate, the title compound was prepared as a solid. MS [M+H]$^+$ 470.0

EXAMPLE 16

Preparation of 1-[1-(3,4-Dichloro-phenyl)-methanoyl]-5-(3-fluoro-phenyl)-2-isobutyl-pyrrolidine-2,4-dicarboxylic acid Following the procedure of Example 3, except substituting tert-butyl acrylate (0.5 mL) for methyl acrylate, the title compound was prepared as a solid. MS [M+H]$^+$481.8

EXAMPLE 17

Preparation of 1-[1-(3,4-Dichloro-phenyl)-methanoyl]-2-isobutyl-5-(3-methoxy-phenyl)-pyrrolidine-2,4-dicarboxylic acid Following the procedure of Example 5, except substituting tert-butyl acrylate (0.5 mL) for methyl acrylate, the title compound was prepared as a solid. MS [M+H]$^+$494.0

EXAMPLE 18

Preparation of 5-(2-Chloro-5-trifluoromethyl-phenyl)-1-[1-(3,4-dichloro-phenyl)-methanoyl]-2-isobutyl-pyrrolidine-2,4-dicarboxylic acid Following the procedure of Example 7, except substituting tert-butyl acrylate (0.5 mL) for methyl acrylate, the title compound was prepared as a solid. MS [M+H]$^+$566.0

EXAMPLE 19

Preparation of 5-(2-Chloro-5-trifluoromethyl-phenyl)-2-isobutyl-1-[1-(4-trifluoromethyl-phenyl)-methanoyl]-pyrrolidine-2,4-dicarboxylic acid Following the procedure of Example 6, except substituting tert-butyl acrylate (0.5 mL) for methyl acrylate, the title compound was prepared as a solid. MS [M+H]$^+$566.0

EXAMPLE 20

Preparation of 1-[1-(3,4-Dichloro-phenyl)-methanoyl]-2-isobutyl-5-(2,3,5-trichloro-phenyl)-pyrrolidine-2,4-dicarboxylic acid Following the procedure of Example 1(a)–1(d), except substituting tert-butyl acrylate (0.5 mL) for methyl acrylate and 2,3,5 trichlorobenzaldehyde for thiophene-2-carboxaldehyde, the title compound was prepared as a solid. MS [M+H]$^+$568.0

EXAMPLE 21

Preparation of 5-(3-Bromo-4,5-dimethoxy-phenyl)-2-methyl-1-[1-(4-trifluoromethyl-phenyl)-methanoyl]-pyrrolidine-2,4 dicarboxylic acid Following the procedure of Example, 14, except substituting tert-butyl acrylate (0.5 mL) for methyl acrylate, the title compound was prepared as a solid. MS [M+H]$^+$562.0

EXAMPLE 22

Preparation of 2-Benzyl-5-thiophen-2-yl-1-[1-(4-trifluoromethyl-phenyl)-methanoyl]-pyrrolidine-2,4-dicarboxylic acid Following the procedure of Example 9, except substituting tert-butyl acrylate (0.5 mL) for methyl acrylate, the title compound was prepared as a solid. MS [M+H]$^+$504.0

EXAMPLE 23

Preparation of 2-Benzyl-1-[1-(3,4-dichloro-phenyl)-methanoyl]-5-(3-fluoro-phenyl)-pyrrolidine-2,4-dicarboxylic acid Following the procedure of Example 12, except substituting tert-butyl acrylate (0.5 mL) for methyl acrylate, the title compound was prepared as a solid. MS [M+H]$^+$516.0

EXAMPLE 24

Preparation of 2-Benzyl-5-(3-fluoro-phenyl)-1-[1-(4-trifluoromethyl-phenyl)-methanoyl]-pyrrolidine-2,4-dicarboxylic acid Following the procedure of Example 11, except substituting tert-butyl acrylate (0.5 mL) for methyl acrylate, the title compound was prepared as a solid. MS [M+H]$^+$516.0

EXAMPLE 25

Preparation of 2-Benzyl-5-(3-methoxy-phenyl)-1-[1-(4-trifluoromethyl-phenyl)-methanoyl]-pyrrolidine-2,4-dicarboxylic acid Following the procedure of Example 13, except substituting tert-butyl acrylate (0.5 mL) for methyl acrylate, the title compound was prepared as a solid. MS [M+H]$^+$528.0

EXAMPLE 26

Preparation of 2-Benzyl-5-(2-chloro-5-trifluoromethyl-phenyl)-1-[1-(4-trifluoromethyl-phenyl)-methanoyl]-pyrrolidine-2,4-dicarboxylic acid Following the procedure of Example 8, except substituting tert-butyl acrylate (0.5 mL) for methyl acrylate, the title compound was prepared as a solid. MS [M+H]$^+$600.0

EXAMPLE 27

Preparation of 2-Benzyl-1-[1-(3,4-dichloro-phenyl)-methanoyl]-5-(2,3,5-trichloro-phenyl)-pyrrolidine-2, 4-dicarboxylic acid Following the procedure of Example 9, except substituting tert-butyl acrylate (0.5 mL) for methyl acrylate and 2,3,5 trichlorobenzaldehyde for thiophene-2-carboxaldehyde, the title compound was prepared as a solid. MS [M+H]⁺601.8

Also included in the present invention is a process according to Scheme 2 for the synthesis of the compounds using a suitable solid phase such as Wang, Merrifield, BAL or other suitable resin.

c) Wang resin bound-1-[1-(3,4-Dichloro-phenyl)-methanoyl]-2-isobutyl-5-thiophen-2-ylpyrrolidine-2,4-dicarboxylic acid 4-tert-butyl ester The compound of Example 28(b) (0.1 gm, 0.086 mmol) was suspended in acetonitrile (2 mL) and treated with 3,4-dichlorobenzoyl chloride (5 eq., 0.09 g) and triethy-

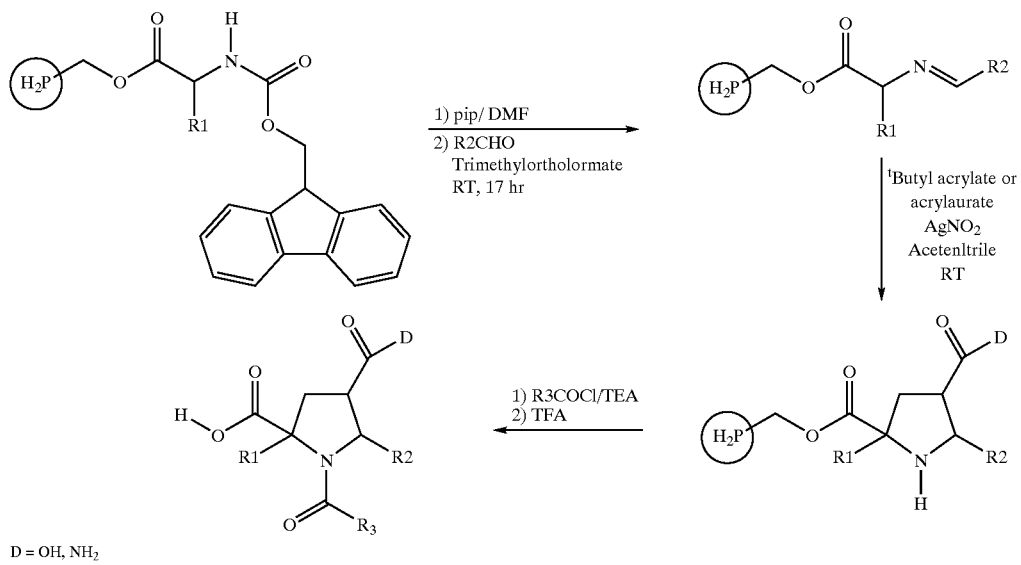

Scheme 1

D = OH, NH₂

With appropriate manipulation and protection of any chemical functionality, synthesis of the remaining compounds of Formula (I) is accomplished by methods analogous to those above and to those described in the Experimental section below:

EXAMPLE 28

Preparation of 1-[1-(3,4-Dichloro-phenyl)-methanoyl]-2-isobutyl-5-thiophen-2-yl-pyrrolidine-2,4-dicarboxylic acid a) Wang resin bound -4-Methyl-2-[(thiophen-2-ylmethylene)-amino]-pentanoic acid Wang bound Fmoc-L-leucine (5.0 gm, 0.86 mmol/gm loading) was suspended in a 20% piperidine/dimethylformamide solution (10 mL) and shaken for 20 minutes. The solution was decanted from the resin and the resin treated again with a second fresh solution (10 mL) for 30 minutes. The resin was filtered and washed successively with dimethylformamide x3, tetrahydrofuran x4, dichloromethane x4, and methanol x4.

A portion of the resin (0.1 gm, 0.088 mmol) was suspended in Trimethylorthoformate (2 mL) and treated with thiophene-2-carboxaldehyde (10 eq., 0.08 mL). The mixture was shaken for 16 hours at room temperature on a wrist shaker. The mixture was filtered and washed successively with tetrahydrofuran x4, and dichloromethane x8.

b) Wang resin bound-2-Isobutyl-5-thiophen-2-yl-pyrrolidine-2,4-dicarboxylic acid 4-tert-butyl ester The compound of Example 28(a) (0.1 gm, 0.086 mmol) was suspended in acetonitrile (2 mL). The mixture was treated with tert-butyl acrylate (3 eq., 0.038 mL), silver nitrate (3.5 eq, 51 mg), and triethylamine (3.5 eq, 0.042 ml). The mixture was shaken for 16 hours at room temperature on a wrist shaker. The mixture was filtered and washed successively with tetrahydrofuran x4, and dichloromethane x8.

lamine (5 eq, 0.06 mL). The mixture was shaken for 16 hours at room temperature on a wrist shaker. The mixture was filtered and washed successively with tetrahydrofuran x4, and dichloromethane x8.

d) 1-[1-(3,4-Dichloro-phenyl)-methanoyl]-2-isobutyl-5-thiophen-2-yl-pyrrolidine-2,4-dicarboxylic acid The compound of Example 28(c) was treated with neat trifluoroacetic acid for 5 hours. The solution was removed from the resin and the resin washed with dichloromethane x3. The TFA solution and washes were combined and evaporated. The residue was chromatographed using Gilson reverse phase HPLC to give the desired compound as a solid (21.2 mg). MS [M+H]⁺471.4

EXAMPLE 29

Preparation of 2-(2-Carbamoyl-ethyl)-5-thiophen-2-yl-1-[1-(4-trifluoromethyl-phenyl)-methanoyl]-pyrrolidine-2,4-dicarboxylic acid Following the procedure of Example 28(a)–28(d), except beginning with Wang bound Fmoc-L-glutamine (Trt) instead of Wang bound Fmoc-L-leucine, and substituting 4-trifluoromethyl benzoyl chloride for 3,4-dichlorobenzoyl chloride, the title compound was prepared as a solid. MS [M+H]⁺485.4

EXAMPLE 30

Preparation of 1-[1-(3,4-Dichloro-phenyl)-methanoyl]-2-(3H-imidazol-4-ylmethyl)-5-thiophen-2-yl-pyrrolidine-2,4-dicarboxylic acid Following the procedure of Example 28(a)–28(d), except beginning with Wang bound Fmoc-L-histidine (Trt) instead of Wang bound Fmoc-L-leucine, the title compound was prepared as a solid. MS [M+H]⁺495.4

EXAMPLE 31

Preparation of 2-(3H-Imidazol-4-ylmethyl)-5-thiophen-2-yl-1-[1-(4-trifluoromethyl-phenyl)-methanoyl]-pyrrolidine-2,4-dicarboxylic acid Following the procedure of Example 28(a)–28(d), except beginning with Wang bound Fmoc-L-histidine (Trt) instead of Wang bound Fmoc-L-leucine, and substituting 4-trifluoromethyl benzoyl chloride for 3,4-dichlorobenzoyl chloride, the title compound was prepared as a solid. MS [M+H]$^+$494.4

EXAMPLE 32

Preparation of 2-Isobutyl-1-(1-phenyl-methanoyl)-5-thiophen-2-yl-pyrrolidine-2,4-dicarboxylic acid Following the procedure of Example 28(a)–28(d), except substituting benzoyl chloride for 3,4-dichlorobenzoyl chloride, the title compound was prepared as a solid. MS [M+H]$^+$402.4

EXAMPLE 33

Preparation of 2-Isobutyl-1-(1-phenyl-methanoyl)-5-thiophen-2-yl-pyrrolidine-2,4-dicarboxylic acid Following the procedure of Example 28(a)–28(d), except beginning with Wang bound Fmoc-L-serine (tBu) instead of Wang bound Fmoc-L-leucine, and substituting benzoyl chloride for 3,4-dichlorobenzoyl chloride, the title compound was prepared as a solid. MS [M+H]$^+$376.4

EXAMPLE 34

Preparation of 2-Isobutyl-5-thiophen-2-yl-1-(1-o-tolyl-methanoyl)-pyrrolidine-2,4-dicarboxylic acid Following the procedure of Example 28(a)–28(d), except substituting o-toluoylchloride for 3,4-dichlorobenzoyl chloride, the title compound was prepared as a solid. MS [M+H]$^+$416.5

EXAMPLE 35

Preparation of 1-[1-(4-Chloro-phenyl)-methanoyl]-2-isobutyl-5-thiophen-2-yl-pyrrolidine-2,4-dicarboxylic acid Following the procedure of Example 28(a)–28(d), except substituting 4-chlorobenzoylchloride for 3,4-dichlorobenzoyl chloride, the title compound was prepared as a solid. MS [M+H]$^+$416.5

EXAMPLE 36

Preparation of 5-Benzofuran-2-yl-2-isobutyl-1-[1-(4-trifluoromethyl-phenyl)-methanoyl]-pyrrolidine-2,4-dicarboxylic acid Following the procedure of Example 28(a)–28(d), except substituting benzofuran-2-carboxaldehyde for thiophene-2-carboxaldehyde, and substituting 4-trifluoromethylbenzoyl chloride for 3,4-dichlorobenzoyl chloride, the title compound was prepared as a solid. MS [M+H]$^+$504.4

EXAMPLE 37

Preparation of 5-Benzofuran-2-yl-2-carbamoylmethyl-1-[1-(4-trifluoromethyl-phenyl)-methanoyl]-pyrrolidine-2,4-dicarboxylic acid Following the procedure of Example 28(a)–28(d), except beginning with Wang bound Fmoc-L-asparagine (Trt) instead of Wang bound Fmoc-L-leucine, and substituting benzofuran-2-carboxaldehyde for thiophene-2-carboxaldehyde, and substituting 4-trifluoromethylbenzoyl chloride for 3,4-dichlorobenzoyl chloride, the title compound was prepared as a solid. MS [M+H]$^+$505.4

EXAMPLE 38

Preparation of 5-Benzofuran-2-yl-2-(2-carbamoyl-ethyl)-1-[1-(4-trifluoromethyl-phenyl)-methanoyl]-pyrrolidine-2,4-dicarboxylic acid Following the procedure of Example 28(a)–28(d), except beginning with Wang bound Fmoc-L-glutamine (Trt) instead of Wang bound Fmoc-L-leucine, and substituting benzofuran-2-carboxaldehyde for thiophene-2-carboxaldehyde, and substituting 4-trifluoromethylbenzoyl chloride for 3,4-dichlorobenzoyl chloride, the title compound was prepared as a solid. MS [M+H]$^+$518.4

EXAMPLE 39

Preparation of 5-Benzofuran-2-yl-2-(3H-imidazol-4-ylmethyl)-1-[1-(4-trifluoromethyl-phenyl)-methanoyl]-pyrrolidine-2,4-dicarboxylic acid Following the procedure of Example 28(a)–28(d), except beginning with Wang bound Fmoc-L-histidine (Trt) instead of Wang bound Fmoc-L-leucine, and substituting benzofuran-2-carboxaldehyde for thiophene-2-carboxaldehyde, and substituting 4-trifluoromethylbenzoyl chloride for 3,4-dichlorobenzoyl chloride, the title compound was prepared as a solid. MS [M+H]$^+$528.4

EXAMPLE 40

Preparation of 5-Benzofuran-2-yl-2-hydroxymethyl-1-[1-(4-trifluoromethyl-phenyl)-methanoyl]-pyrrolidine-2,4-dicarboxylic acid Following the procedure of Example 28(a)–28(d), except beginning with Wang bound Fmoc-L-serine (tBu) instead of Wang bound Fmoc-L-leucine, and substituting benzofuran-2-carboxaldehyde for thiophene-2-carboxaldehyde, and substituting 4-trifluoromethylbenzoyl chloride for 3,4-dichlorobenzoyl chloride, the title compound was prepared as a solid. MS [M+H]$^+$478.4

EXAMPLE 41

Preparation of 2-Isobutyl-1-(1-naphthalen-1-yl-methanoyl)-5-thiophen-2-yl- pyrrolidine-2,4-dicarboxylic acid Following the procedure of Example 28(a)–28(d), except substituting 1-naphthoyl chloride for 3,4-dichlorobenzoyl chloride, the title compound was prepared as a solid. MS [M+H]$^+$452.5

EXAMPLE 42

Preparation of 5-Furan-2-yl-2-isobutyl-1-[1-(4-trifluoromethyl-phenyl)-methanoyl]-pyrrolidine-2,4-dicarboxylic acid Following the procedure of Example 28(a)–28(d), except substituting furan-2-carboxaldehyde for thiophene-2-carboxaldehyde, and substituting 4-trifluoromethylbenzoyl chloride for 3,4-dichlorobenzoyl chloride, the title compound was prepared as a solid. MS [M+H]$^+$454.4

EXAMPLE 43

Preparation of 5-[5-(4-Chloro-phenyl)-furan-2-yl]-2-isobutyl-1-[1-(4-trifluoromethyl-phenyl)-methanoyl]-pyrrolidine-2,4-dicarboxylic acid Following the procedure of Example 28(a)–28(d), except substituting 5-(4-chloro-phenyl)-furan-2-carboxaldehyde for thiophene-2-carboxaldehyde, and substituting 4-trifluoromethyl benzoylchloride for 3,4-dichlorobenzoyl chloride, the title compound was prepared as a solid. MS $[M+H]^+$564.9

EXAMPLE 44

Preparation of 5-[5-(4-Chloro-phenyl)-furan-2-yl]-2-isobutyl-1-[1-(4-trifluoromethyl-phenyl)-methanoyl]-pyrrolidine-2,4-dicarboxylic acid Following the procedure of Example 28(a)–28(d), except substituting thiazole-2-carboxaldehyde for thiophene-2-carboxaldehyde, and substituting 4-trifluoromethylbenzoyl chloride for 3,4-dichlorobenzoyl chloride, the title compound was prepared as a solid. MS $[M+H]^+$471.4

EXAMPLE 45

Preparation of 2-(2-Carbamoyl-ethyl)-5-furan-2-yl-1-(1-o tolyl-methanoyl)-pyrrolidine-2,4-dicarboxylic acid Following the procedure of Example 28(a)–28(d), except beginning with Wang bound Fmoc-L-glutamine (Trt) instead of Wang bound Fmoc-L-leucine, and substituting furan-2-carboxaldehyde for thiophene-2-carboxaldehyde, and substituting o-toluoyl chloride for 3,4-dichlorobenzoyl chloride, the title compound was prepared as a solid. MS $[M+H]^+$ 415.4

EXAMPLE 46

Preparation of 5-Furan-2-yl-2-hydroxymethyl-1-(1-o-tolyl-methanoyl)-pyrrolidine-2,4-dicarboxylic acid Following the procedure of Example 28(a)–28(d), except beginning with Wang bound Fmoc-L-serine (tBu) instead of Wang bound Fmoc-L-leucine, and substituting furan-2-carboxaldehyde for thiophene-2-carboxaldehyde, and substituting o-toluoyl chloride for 3,4-dichlorobenzoyl chloride, the title compound was prepared as a solid. MS $[M+H]^+$ 374.3

EXAMPLE 47

Preparation of 5-Furan-2-yl-2-(1H-imidazol-4-ylmethyl)-1-(1-o-tolyl-methanoyl)-pyrrolidine-2,4-dicarboxylic acid Following the procedure of Example 28(a)–28(d), except beginning with Wang bound Fmoc-L-histidine (Trt) instead of Wang bound Fmoc-L-leucine, and substituting furan-2-carboxaldehyde for thiophene-2-carboxaldehyde, and substituting o-toluoyl chloride for 3,4-dichlorobenzoyl chloride, the title compound was prepared as a solid. MS $[M+H]^+$ 424.4

EXAMPLE 48

Preparation of 2-(2-Carbamoyl-ethyl)-5-thiazol-2-yl-1-(1-o-tolyl-methanoyl)-pyrrolidine-2,4-dicarboxylic acid Following the procedure of Example 28(a)–28(d), except beginning with Wang bound Fmoc-L-glutamine (Trt) instead of Wang bound Fmoc-L-leucine, and substituting thiazole-2-carboxaldehyde for thiophene-2-carboxaldehyde, and substituting o-toluoyl chloride for 3,4-dichlorobenzoyl chloride, the title compound was prepared as a solid. MS $[M+H]^+$ 432.4

EXAMPLE 49

Preparation of 2-Hydroxymethyl-5-thiazol-2-yl-1-(1-o-tolyl-methanoyl)-pyrrolidine-2,4-dicarboxylic acid Following the procedure of Example 28(a)–28(d), except beginning with Wang bound Fmoc-L-serine (tBu) instead of Wang bound Fmoc-L-leucine, and substituting thiazole-2-carboxaldehyde for thiophene-2-carboxaldehyde, and substituting o-toluoyl chloride for 3,4-dichlorobenzoyl chloride, the title compound was prepared as a solid. MS $[M+H]^+$ 391.4

EXAMPLE 50

Preparation of 2-(1H-Imidazol-4-ylmethyl)-5-thiazol-2-yl-1-(1-o-tolyl-methanoyl)-pyrrolidine-2,4-dicarboxylic acid Following the procedure of Example 28(a)–28(d), except beginning with Wang bound Fmoc-L-histidine (Trt) instead of Wang bound Fmoc-L-leucine, and substituting thiazole-2-carboxaldehyde for thiophene-2-carboxaldehyde, and substituting o-toluoyl chloride for 3,4-dichlorobenzoyl chloride, the title compound was prepared as a solid. MS $[M+H]^+$ 441.4

EXAMPLE 51

Preparation of 2-(2-Carbamoyl-ethyl)-5-[5-(4-chloro-phenyl)-furan-2-yl]-1-(1-o-tolyl-methanoyl)-pyrrolidine-2,4-dicarboxylic Acid Following the procedure of Example 28(a)–28(d), except beginning with Wang bound Fmoc-L-glutamine (Trt) instead of Wang bound Fmoc-L-leucine, and substituting 5-(4-chloro-phenyl)-furan-2-carboxaldehyde for thiophene-2-carboxaldehyde, and substituting o-toluoyl chloride for 3,4-dichlorobenzoyl chloride, the title compound was prepared as a solid. MS $[M+H]^+$525.9

EXAMPLE 52

Preparation of 5-[5-(4-Chloro-phenyl)-furan-2-yl]-2-hydroxymethyl-1-(1-o-tolyl-methanoyl)-pyrrolidine-2,4-dicarboxylic Acid Following the procedure of Example 28(a)–28(d), except beginning with Wang bound Fmoc-L-serine (tBu) instead of Wang bound Fmoc-L-leucine, and substituting 5-(4-chloro-phenyl)-furan-2-carboxaldehyde for thiophene-2-carboxaldehyde, and substituting o-toluoyl chloride for 3,4-dichlorobenzoyl chloride, the title compound was prepared as a solid. MS $[M+H]^+$484.9

EXAMPLE 53

Preparation of 5-[5-(4-Chloro-phenyl)-furan-2-yl]-2-(1H-imidazol-4-ylmethyl)-1-(1-o-tolyl-methanoyl)-pyrrolidine-2,4-dicarboxylic Acid Following the procedure of Example 28(a)–28(d), except beginning with Wang bound Fmoc-L-histidine (Trt) instead of Wang bound Fmoc-L-leucine, and substituting 5-(4-chloro-phenyl)-furan-2-carboxaldehyde for thiophene-2-carboxaldehyde, and substituting o-toluoyl chloride for 3,4-dichlorobenzoyl chloride, the title compound was prepared as a solid. MS [M+H]$^+$534.9

EXAMPLE 54

Preparation of 2-(2-Carbamoyl-ethyl)-5-thiophen-2-yl-1-(1-o-tolyl-methanoyl)-pyrrolidine-2,4-dicarboxylic Acid Following the procedure of Example 28(a)–28(d), except beginning with Wang bound Fmoc-L-glutamine (Trt) instead of Wang bound Fmoc-L-leucine, and substituting o-toluoyl chloride for 3,4-dichlorobenzoyl chloride, the title compound was prepared as a solid. MS [M+H]$^+$431.4

EXAMPLE 55

Preparation of 2-Hydroxymethyl-5-thiophen-2-yl-1-(1-o-tolyl-methanoyl)-pyrrolidine-2,4-dicarboxylic Acid Following the procedure of Example 28(a)–28(d), except beginning with Wang bound Fmoc-L-serine (tBu) instead of Wang bound Fmoc-L-leucine, and substituting o-toluoyl chloride for 3,4-dichlorobenzoyl chloride, the title compound was prepared as a solid. MS [M+H]$^+$390.4

EXAMPLE 56

Preparation of 2-(1H-Imidazol-4-ylmethyl)-5-thiophen-2-yl-1-(1-o-tolyl-methanoyl)-pyrrolidine-2,4-dicarboxylic Acid Following the procedure of Example 28(a)–28(d), except beginning with Wang bound Fmoc-L-histidine (Trt) instead of Wang bound Fmoc-L-leucine, and substituting o-toluoyl chloride for 3,4-dichlorobenzoyl chloride, the title compound was prepared as a solid. MS [M+H]$^+$440.4

EXAMPLE 57

Preparation of 1-[1-(4-Chloro-phenyl)-methanoyl]-5-furan-2-yl-2-(1H-imidazol-4-ylmethyl)-pyrrolidine-2,4-dicarboxylic Acid Following the procedure of Example 28(a)–28(d), except beginning with Wang bound Fmoc-L-histidine (Trt) instead of Wang bound Fmoc-L-leucine, and substituting furan-2-carboxaldehyde for thiophene-2-carboxaldehyde, and substituting 4-chlorobenzoylchloride for 3,4-dichlorobenzoyl chloride, the title compound was prepared as a solid. MS [M+H]$^+$444.8

EXAMPLE 58

Preparation of 2-(2-Carbamoyl-ethyl)-1-[1-(4-chloro-phenyl)-methanoyl]-5-thiazol-2-yl-pyrrolidine-2,4-dicarboxylic Acid Following the procedure of Example 28(a)–28(d), except beginning with Wang bound Fmoc-L-glutamine (Trt) instead of Wang bound Fmoc-L-leucine, and substituting thiazole-2-carboxaldehyde for thiophene-2-carboxaldehyde, and substituting 4-chlorobenzoylchloride for 3,4-dichlorobenzoyl chloride, the title compound was prepared as a solid. MS [M+H]$^+$452.8

EXAMPLE 59

Preparation of 1-[1-(4-Chloro-phenyl)-methanoyl]-2-hydroxymethyl-5-thiazol-2-yl-pyrrolidine-2,4-dicarboxylic Acid Following the procedure of Example 28(a)–28(d), except beginning with Wang bound Fmoc-L-serine (tBu) instead of Wang bound Fmoc-L-leucine, and substituting thiazole-2-carboxaldehyde for thiophene-2-carboxaldehyde, and substituting 4-chlorobenzoylchloride for 3,4-dichlorobenzoyl chloride, the title compound was prepared as a solid. MS [M+H]$^+$411.8

EXAMPLE 60

Preparation of 1-[1-(4-Chloro-phenyl)-methanoyl]-2-(1H-imidazol-4-ylmethyl)-5-thiazol-2-yl-pyrrolidine-2,4-dicarboxylic Acid Following the procedure of Example 28(a)–28(d), except beginning with Wang bound Fmoc-L-histidine (Trt) instead of Wang bound Fmoc-L-leucine, and substituting thiazole-2-carboxaldehyde for thiophene-2-carboxaldehyde, and substituting 4-chlorobenzoylchloride for 3,4-dichlorobenzoyl chloride, the title compound was prepared as a solid. MS [M+H]$^+$461.8

EXAMPLE 61

Preparation of 5-[5-(4-Chloro-phenyl)-furan-2-yl]-1-[1-(4-chloro-phenyl)-methanoyl]-2-hydroxymethyl-pyrrolidine-2,4-dicarboxylic Acid Following the procedure of Example 28(a)–28(d), except beginning with Wang bound Fmoc-L-serine (tBu) instead of Wang bound Fmoc-L-leucine, and substituting 5-(4-chloro-phenyl)-furan-2-carboxaldehyde for thiophene-2-carboxaldehyde, and substituting 4-chlorobenzoylchloride for 3,4-dichlorobenzoyl chloride, the title compound was prepared as a solid. MS [M+H]$^+$505.3

EXAMPLE 62

Preparation of 2-(2-Carbamoyl-ethyl)-1-[1-(4-chloro-phenyl)-methanoyl]-5-thiophen-2-yl-pyrrolidine-2,4-dicarboxylic Acid Following the procedure of Example 28(a)–28(d), except beginning with Wang bound Fmoc-L-glutamine (Trt) instead of Wang bound Fmoc-L-leucine, and substituting 4-chlorobenzoylchloride for 3,4-dichlorobenzoyl chloride, the title compound was prepared as a solid. MS [M+H]$^+$ 451.8

EXAMPLE 63

Preparation of 5-Furan-2-yl-2-(1H-imidazol-4-ylmethyl)-1-[1-(4-trifluoromethyl-phenyl)-methanoyl]-pyrrolidine-2,4-dicarboxylic Acid Following the procedure of Example 28(a)–28(d), except beginning with Wang bound Fmoc-L-histidine (Trt) instead of Wang bound Fmoc-L-leucine, and substituting furan-2-carboxaldehyde for thiophene-2-carboxaldehyde, and substituting 4-trifluoromethylbenzoyl chloride for 3,4-dichlorobenzoyl chloride, the title compound was prepared as a solid. MS [M+H]$^+$478.3

EXAMPLE 64

Preparation of 2-(2-Carbamoyl-ethyl)-5-thiazol-2-yl-1-[1-(4-trifluoromethyl-phenyl)-methanoyl]-pyrrolidine-2,4-dicarboxylic Acid Following the procedure of Example 28(a)–28(d), except beginning with Wang bound Fmoc-L-glutamine (Trt) instead of Wang bound Fmoc-L-leucine, and substituting thiazole- 2-carboxaldehyde for thiophene-2-carboxaldehyde, and substituting 4-trifluoromethylbenzoyl chloride for 3,4-dichlorobenzoyl chloride, the title compound was prepared as a solid. MS [M+H]$^+$486.4

EXAMPLE 65

Preparation of 2-Hydroxymethyl-5-thiazol-2-yl-1-[1-(4-trifluoromethyl-phenyl)-methanoyl]-pyrrolidine-2,4-dicarboxylic Acid Following the procedure of Example 28(a)–28(d), except beginning with Wang bound Fmoc-L-serine (tBu) instead of Wang bound Fmoc-L-leucine, and substituting thiazole-2-carboxaldehyde for thiophene-2-carboxaldehyde, and substituting 4-trifluoromethylbenzoyl chloride for 3,4-dichlorobenzoyl chloride, the title compound was prepared as a solid. MS [M+H]$^+$445.3

EXAMPLE 66

Preparation of 2-(1H-Imidazol-4-ylmethyl)-5-thiazol-2-yl-1-[1-(4-trifluoromethyl-phenyl)-methanoyl]-pyrrolidine-2,4-dicarboxylic Acid Following the procedure of Example 28(a)–28(d), except beginning with Wang bound Fmoc-L-histidine (Trt) instead of Wang bound Fmoc-L-leucine, and substituting thiazole-2-carboxaldehyde for thiophene-2-carboxaldehyde, and substituting 4-trifluoromethylbenzoyl chloride for 3,4-dichlorobenzoyl chloride, the title compound was prepared as a solid. MS [M+H]$^+$495.4

EXAMPLE 67

Preparation of 5-[5-(4-Chloro-phenyl)-furan-2-yl]-2-hydroxymethyl-1-[1-(4-trifluoromethyl-phenyl)-methanoyl]-pyrrolidine-2,4-dicarboxylic acid Following the procedure of Example 28(a)–28(d), except beginning with Wang bound Fmoc-L-serine (tBu) instead of Wang bound Fmoc-L-leucine, and substituting 5-(4-chloro-phenyl)-furan-2-carboxaldehyde for thiophene-2-carboxaldehyde, and substituting 4-trifluoromethylbenzoyl chloride for 3,4-dichlorobenzoyl chloride, the title compound was prepared as a solid. MS [M+H]$^+$538.8

EXAMPLE 68

Preparation of 5-[5-(4-Chloro-phenyl)-furan-2-yl]-2-(1H-imidazol-4-ylmethyl)-1-[1-(4-trifluoromethyl-phenyl)-methanoyl]-pyrrolidine-2,4-dicarboxylic Acid Following the procedure of Example 28(a)–28(d), except beginning with Wang bound Fmoc-L-histidine (Trt) instead of Wang bound Fmoc-L-leucine, and substituting 5-(4-chloro-phenyl)-furan-2-carboxaldehyde for thiophene-2-carboxaldehyde, and substituting 4-trifluoromethylbenzoyl chloride for 3,4-dichlorobenzoyl chloride, the title compound was prepared as a solid. MS [M+H]$^+$588.9

EXAMPLE 69

Preparation of 2-(2-Carbamoyl-ethyl)-1-(1-naphthalen-1-yl-methanoyl)-5-thiazol-2-yl-pyrrolidine-2,4-dicarboxylic Acid Following the procedure of Example 28(a)–28(d), except beginning with Wang bound Fmoc-L-glutamine (Trt) instead of Wang bound Fmoc-L-leucine, and substituting thiazole-2-carboxaldehyde for thiophene-2-carboxaldehyde, and substituting 1-naphthoyl chloride for 3,4-dichlorobenzoyl chloride, the title compound was prepared as a solid. MS [M+H]$^+$468.5

EXAMPLE 70

Preparation of 2-Hydroxymethyl-1-(1-naphthalen-1-yl-methanoyl)-5-thiazol-2-yl-pyrrolidine-2,4-dicarboxylic Acid Following the procedure of Example 28(a)–28(d), except beginning with Wang bound Fmoc-L-serine (tBu) instead of Wang bound Fmoc-L-leucine, and substituting thiazole-2-carboxaldehyde for thiophene-2-carboxaldehyde, and substituting 1-naphthoyl chloride for 3,4-dichlorobenzoyl chloride, the title compound was prepared as a solid. MS [M+H]$^+$427.4

EXAMPLE 71

Preparation of 2-(1H-Imidazol-4-ylmethyl)-1-(1-naphthalen-1-yl-methanoyl)-5-thiazol-2-yl-pyrrolidine-2,4-dicarboxylic Acid Following the procedure of Example 28(a)–28(d), except beginning with Wang bound Fmoc-L-histidine (Trt) instead of Wang bound Fmoc-L-leucine, and substituting thiazole-2-carboxaldehyde for thiophene-2-carboxaldehyde, and substituting 1-naphthoyl chloride for 3,4-dichlorobenzoyl chloride, the title compound was prepared as a solid. MS [M+H]$^+$477.5

EXAMPLE 72

Preparation of 2-(2-Carbamoyl-ethyl)-5-[5-(4-chloro-phenyl)-furan-2-yl]-1-(1-naphthalen-1-yl-methanoyl)-pyrrolidine-2,4-dicarboxylic Acid Following the procedure of Example 28(a)–28(d), except beginning with Wang bound Fmoc-L-glutamine (Trt) instead of Wang bound Fmoc-L-leucine, and substituting 5-(4-chloro-phenyl)-furan-2-carboxaldehyde for thiophene-2-carboxaldehyde, and substituting 1-naphthoyl chloride for 3,4-dichlorobenzoyl chloride, the title compound was prepared as a solid. MS [M+H]$^+$561.9

EXAMPLE 73

Preparation of 5-[5-(4-Chloro-phenyl)-furan-2-yl]-2-(1H-imidazol-4-ylmethyl)-1-(1-naphthalen-1-yl-methanoyl)-pyrrolidine-2,4-dicarboxylic Acid Following the procedure of Example 28(a)–28(d), except beginning with Wang bound Fmoc-L-histidine (Trt) instead of Wang bound Fmoc-L-leucine, and substituting 5-(4-chloro-phenyl)-furan-2-carboxaldehyde for thiophene-2-carboxaldehyde, and substituting 1-naphthoyl chloride for 3,4-dichlorobenzoyl chloride, the title compound was prepared as a solid. MS [M+H]$^+$570.9

EXAMPLE 74

Preparation of 2-(2-Carbamoyl-ethyl)-1-(1-naphthalen-1-yl-methanoyl)-5-thiophen-2-yl-pyrrolidine-2,4-dicarboxylic Acid Following the procedure of Example 28(a)–28(d), except beginning with Wang bound Fmoc-L-glutamine (Trt) instead of Wang bound Fmoc-L-leucine, and substituting 1-naphthoyl chloride for 3,4-dichlorobenzoyl chloride, the title compound was prepared as a solid. MS [M+H]$^+$467.5

EXAMPLE 75

Preparation of 2-Hydroxymethyl-1-(1-naphthalen-1-yl-methanoyl)-5-thiophen-2-yl-pyrrolidine-2,4-dicarboxylic Acid Following the procedure of Example 28(a)–28(d), except beginning with Wang bound Fmoc-L-serine (tBu) instead of Wang bound Fmoc-L-leucine, and substituting 1-naphthoyl chloride for 3,4-dichlorobenzoyl chloride, the title compound was prepared as a solid. MS [M+H]$^+$426.4

EXAMPLE 76

Preparation of 2-(1H-Imidazol-4-ylmethyl)-1-(1-naphthalen-1-yl-methanoyl)-5-thiophen-2-yl-pyrrolidine-2,4-dicarboxylic Acid Following the procedure of Example 28(a)–28(d), except beginning with Wang bound Fmoc-L-histidine (Trt) instead of Wang bound Fmoc-L-leucine, and substituting 1-naphthoyl chloride for 3,4-dichlorobenzoyl chloride, the title compound was prepared as a solid. MS [M+H]$^+$476.5

EXAMPLE 77

Preparation of 2-Isobutyl-5-thiophen-3-yl-1-[1-(4-trifluoromethyl-phenyl)-methanoyl]-pyrrolidine-2,4-dicarboxylic Acid Following the procedure of Example 28(a)–28(d), except substituting thiophene-3-carboxaldehyde for thiophene-2-carboxaldehyde, and substituting 4-trifluoromethylbenzoyl chloride for 3,4-dichlorobenzoyl chloride, the title compound was prepared as a solid. MS [M+H]$^+$470.4

EXAMPLE 78

Preparation of 5-Furan-3-yl-2-isobutyl-1-[1-(4-trifluoromethyl-phenyl)-methanoyl]-pyrrolidine-2,4-dicarboxylic Acid Following the procedure of Example 28(a)–28(d), except substituting furan-3-carboxaldehyde for thiophene-2-carboxaldehyde, and substituting 4-trifluoromethylbenzoyl chloride for 3,4-dichlorobenzoyl chloride, the title compound was prepared as a solid. MS [M+H]$^+$454.4

EXAMPLE 79

Preparation of 2-Isobutyl-5-pyridin-2-yl-1-[1-(4-trifluoromethyl-phenyl)-methanoyl]-pyrrolidine-2,4-dicarboxylic Acid Following the procedure of Example 28(a)–28(d), except substituting pyridine-2-carboxaldehyde for thiophene-2-carboxaldehyde, and substituting 4-trifluoromethylbenzoyl chloride for 3,4-dichlorobenzoyl chloride, the title compound was prepared as a solid. MS [M+H]$^+$465.4

EXAMPLE 80

Preparation of 5-(5-Ethyl-furan-2-yl)-2-isobutyl-1-[1-(4-trifluoromethyl-phenyl)-methanoyl]-pyrrolidine-2,4-dicarboxylic Acid Following the procedure of Example 28(a)–28(d), except substituting 5-Ethyl-furan-2-carboxaldehyde for thiophene-2-carboxaldehyde, and substituting 4-trifluoromethylbenzoyl chloride for 3,4-dichlorobenzoyl chloride, the title compound was prepared as a solid. MS [M+H]$^+$482.4

EXAMPLE 81

Preparation of 2-Isobutyl-5-thiazol-2-yl-1-(1-p-tolyl-methanoyl)-pyrrolidine-2,4-dicarboxylic Acid Following the procedure of Example 28(a)–28(d), except substituting thiazole-2-carboxaldehyde for thiophene-2-carboxaldehyde, and substituting p-toluoyl chloride for 3,4-dichlorobenzoyl chloride, the title compound was prepared as a solid. MS [M+H]$^+$417.4

EXAMPLE 82

Preparation of 5-Benzofuran-2-yl-2-isobutyl-1-(1-p-tolyl-methanoyl)-pyrrolidine-2,4-dicarboxylic Acid Following the procedure of Example 28(a)–28(d), except substituting benzofuran-2-carboxaldehyde for thiophene-2-carboxaldehyde, and substituting p-toluoyl chloride for 3,4-dichlorobenzoyl chloride, the title compound was prepared as a solid. MS [M+H]$^+$450.5

EXAMPLE 83

Preparation of 1-[1-(4-tert-Butyl-phenyl)-methanoyl]-2-isobutyl-5-thiophen-2-yl-pyrrolidine-2,4-dicarboxylic Acid Following the procedure of Example 28(a)–28(d), except substituting 4-t-butylbenzoyl chloride for 3,4-dichlorobenzoyl chloride, the title compound was prepared as a solid. MS [M+H]$^+$458.5

EXAMPLE 84

Preparation of 1-[1-(4-Ethyl-phenyl)-methanoyl]-2-isobutyl-5-thiophen-2-yl-pyrrolidine-2,4-dicarboxylic Acid Following the procedure of Example 28(a)–28(d), except substituting 4-ethylbenzoyl chloride for 3,4-dichlorobenzoyl chloride, the title compound was prepared as a solid. MS [M+H]$^+$430.5

EXAMPLE 85

Preparation of 1-(1-Biphenyl-4-yl-methanoyl)-2-isobutyl-5-thiophen-2-yl-pyrrolidine-2,4-dicarboxylic Acid Following the procedure of Example 28(a)–28(d), except substituting 4-biphenylcarbonyl chloride for 3,4-dichlorobenzoyl chloride, the title compound was prepared as a solid. MS [M+H]$^+$478.5

EXAMPLE 86

Preparation of 1-[1-(3-Chloro-phenyl)-methanoyl]-2-isobutyl-5-thiophen-2-yl-pyrrolidine-2,4-dicarboxylic Acid Following the procedure of Example 28(a)–28(d), except substituting 3-chlorobenzoyl chloride for 3,4-dichlorobenzoyl chloride, the title compound was prepared as a solid. MS [M+H]$^+$436.9

EXAMPLE 87

Preparation of 1-[1-(3-Bromo-phenyl)-methanoyl]-2-isobutyl-5-thiophen-2-yl-pyrrolidine-2,4-dicarboxylic Acid Following the procedure of Example 28(a)–28(d), except substituting 3-bromobenzoyl chloride for 3,4- dichlorobenzoyl chloride, the title compound was prepared as a solid. MS [M+H]$^+$481.3

EXAMPLE 88

Preparation of 2-Isobutyl-5-thiophen-2-yl-1-(1-m-tolyl-methanoyl)-pyrrolidine-2,4-dicarboxylic Acid Following the procedure of Example 28(a)–28(d), except substituting m-toluoyl chloride for 3,4-dichlorobenzoyl chloride, the title compound was prepared as a solid. MS [M+H]$^+$416.5

EXAMPLE 89

Preparation of 1-[1-(3,4-Difluoro-phenyl)-methanoyl]-2-isobutyl-5-thiophen-2-yl-pyrrolidine-2,4-dicarboxylic Acid Following the procedure of Example 28(a)–28(d), except substituting 3,4-difluorobenzoyl chloride for 3,4-dichlorobenzoyl chloride, the title compound was prepared as a solid. MS [M+H]$^+$438.4

EXAMPLE 90

Preparation of 1-[1-(4-Fluoro-phenyl)-methanoyl]-2-isobutyl-5-thiophen-2-yl-pyrrolidine-2,4-dicarboxylic Acid Following the procedure of Example 28(a)–28(d), except substituting 4-fluorobenzoyl chloride for 3,4-dichlorobenzoyl chloride, the title compound was prepared as a solid. MS [M+H]$^+$420.4

EXAMPLE 91

Preparation of 5-Furan-2-yl-2-isobutyl-1-(1-p-tolyl-methanoyl)-pyrrolidine-2,4-dicarboxylic Acid Following the procedure of Example 28(a)–28(d), except substituting furan-2-carboxaldehyde for thiophene-2-carboxaldehyde, and substituting p-toluoyl chloride for 3,4-dichlorobenzoyl chloride, the title compound was prepared as a solid. MS [M+H]$^+$400.4

EXAMPLE 92

Preparation of 1-[1-(4-Chloro-phenyl)-methanoyl]-2-hydroxymethyl-5-thiophen-2-yl-pyrrolidine-2,4-dicarboxylic Acid Following the procedure of Example 28(a)–28(d), except beginning with Wang bound Fmoc-L-serine (tBu) instead of Wang bound Fmoc-L-leucine, and substituting 4-chlorobenzoyl chloride for 3,4-dichlorobenzoyl chloride, the title compound was prepared as a solid. MS [M+H]$^+$410.8

EXAMPLE 93

Preparation of 2-Hydroxymethyl-5-thiophen-2-yl-1-[1-(4-trifluoromethyl-phenyl)-methanoyl]-pyrrolidine-2,4-dicarboxylic Acid Following the procedure of Example 28(a)–28(d), except beginning with Wang bound Fmoc-L-serine (tBu) instead of Wang bound Fmoc-L-leucine, and substituting 4-trifluromethylbenzoyl chloride for 3,4-dichlorobenzoyl chloride, the title compound was prepared as a solid. MS [M+H]$^+$444.3

EXAMPLE 94

Preparation of 2-Carbamoylmethyl-1-(1-naphthalen-1-yl-methanoyl)-5-thiazol-2-yl-pyrrolidine-2,4-dicarboxylic Acid Following the procedure of Example 28(a)–28(d), except beginning with Wang bound Fmoc-L-asparagine (Trt) instead of Wang bound Fmoc-L-leucine, and substituting thiazole-2-carboxaldehyde for thiophene-2-carboxaldehyde, and substituting 1-naphthoyl chloride for 3,4-dichlorobenzoyl chloride, the title compound was prepared as a solid. MS [M+H]$^+$454.4

EXAMPLE 95

Preparation of 1-[1-(Bis-trifluoromethyl-phenyl)-methanoyl]-2-isobutyl-5-thiophen-2-yl-pyrrolidine-2,4-dicarboxylic Acid Following the procedure of Example 28(a)–28(d), except substituting 2,5-bistrifluoromethylbenzoyl chloride for 3,4-dichlorobenzoyl chloride, the title compound was prepared as a solid. MS [M+H]$^+$538.4

EXAMPLE 96

Preparation of 1-[1-(Bis-trifluoromethyl-phenyl)-methanoyl]-2-isobutyl-5-thiophen-2-yl-pyrrolidine-2,4-dicarboxylic Acid Following the procedure of Example 28(a)–28(d), except substituting 3,5-bistrifluoromethylbenzoyl chloride for 3,4-dichlorobenzoyl chloride, the title compound was prepared as a solid. MS [M+H]$^+$538.4

EXAMPLE 97

Preparation of 2-Isobutyl-5-thiazol-2-yl-1-[1-(3-trifluoromethyl-phenyl)-methanoyl]-pyrrolidine-2,4-dicarboxylic Acid Following the procedure of Example 28(a)–28(d), except substituting thiazole-2-carboxaldehyde for thiophene-2-carboxaldehyde, and substituting 3-trifluoromethylbenzoyl chloride for 3,4-dichlorobenzoyl chloride, the title compound was prepared as a solid. MS [M+H]$^+$471.4

EXAMPLE 98

Preparation of 1-[1-(3,4-Dichloro-phenyl)-methanoyl]-2-isobutyl-5-thiazol-2-yl-pyrrolidine-2,4-dicarboxylic Acid Following the procedure of Example 28(a)–28(d), except substituting thiazole-2-carboxaldehyde for thiophene-2-carboxaldehyde, the title compound was prepared as a solid. MS [M+H]$^+$472.4

EXAMPLE 99

Preparation of 1-[1-(3-Bromo-phenyl)-methanoyl]-2-isobutyl-5-thiazol-2-yl-pyrrolidine-2,4-dicarboxylic Acid Following the procedure of Example 28(a)–28(d), except substituting thiazole-2-carboxaldehyde for thiophene-2-carboxaldehyde, and substituting 3-bromobenzoyl chloride for 3,4-dichlorobenzoyl chloride, the title compound was prepared as a solid. MS [M+H]$^+$482.3

EXAMPLE 100

Preparation of 1-[1-(4-Ethyl-phenyl)-methanoyl]-2-isobutyl-5-thiazol-2-yl-pyrrolidine-2,4-dicarboxylic Acid Following the procedure of Example 28(a)–28(d), except substituting thiazole-2-carboxaldehyde for thiophene-2- carboxaldehyde, and substituting 4-ethylbenzoyl chloride for 3,4-dichlorobenzoyl chloride, the title compound was prepared as a solid. MS [M+H]$^+$431.5

EXAMPLE 101

Preparation of 1-[1-(4-tert-Butyl-phenyl)-methanoyl]-2-isobutyl-5-thiazol-2-yl-pyrrolidine-2,4-dicarboxylic Acid Following the procedure of Example 28(a)–28(d), except substituting thiazole-2-carboxaldehyde for thiophene-2-carboxaldehyde, and substituting 4-t-butylbenzoyl chloride for 3,4-dichlorobenzoyl chloride, the title compound was prepared as a solid. MS [M+H]$^+$459.5

EXAMPLE 102

Preparation of 5-Furan-2-yl-2-isobutyl-1-[1-(3-trifluoromethyl-phenyl)-methanoyl]-pyrrolidine-2,4-dicarboxylic Acid Following the procedure of Example 28(a)–28(d), except substituting furan-2-carboxaldehyde for thiophene-2-carboxaldehyde, and substituting 3-trifluoromethylbenzoyl chloride for 3,4-dichlorobenzoyl chloride, the title compound was prepared as a solid. MS [M+H]$^+$454.4

EXAMPLE 103

Preparation of 1-[1-(3,4-Dichloro-phenyl)-methanoyl]-5-furan-2-yl-2-isobutyl-pyrrolidine-2,4-dicarboxylic Acid Following the procedure of Example 28(a)–28(d), except substituting furan-2-carboxaldehyde for thiophene-2-carboxaldehyde, the title compound was prepared as a solid. MS [M+H]$^+$455.3

EXAMPLE 104

Preparation of 1-[1-(3-Bromo-phenyl)-methanoyl]-5-furan-2-yl-2-isobutyl-pyrrolidine-2,4-dicarboxylic Acid Following the procedure of Example 28(a)–28(d), except substituting furan-2-carboxaldehyde for thiophene-2-carboxaldehyde, and substituting 3-bromobenzoyl chloride for 3,4-dichlorobenzoyl chloride, the title compound was prepared as a solid. MS [M+H]$^+$465.3

EXAMPLE 105

Preparation of 5-Benzofuran-2-yl-2-isobutyl-1-[1-(3-trifluoromethyl-phenyl)-methanoyl]-pyrrolidine-2,4-dicarboxylic Acid Following the procedure of Example 28(a)–28(d), except substituting benzofuran-2-carboxaldehyde for thiophene-2-carboxaldehyde, and substituting 3-trifluoromethylbenzoyl chloride for 3,4-dichlorobenzoyl chloride, the title compound was prepared as a solid. MS [M+H]$^+$504.4

EXAMPLE 106

Preparation of 5-Benzofuran-2-yl-1-[1-(3,4-dichloro-phenyl)-methanoyl]-2-isobutyl-pyrrolidine-2,4-dicarboxylic Acid Following the procedure of Example 28(a)–28(d), except substituting benzofuran-2-carboxaldehyde for thiophene-2-carboxaldehyde, the title compound was prepared as a solid. MS [M+H]$^+$505.3

EXAMPLE 107

Preparation of 5-Benzofuran-2-yl-1-[1-(3-bromo-phenyl)-methanoyl]-2-isobutyl-pyrrolidine-2,4-dicarboxylic Acid Following the procedure of Example 28(a)–28(d), except substituting benzofuran-2-carboxaldehyde for thiophene-2-carboxaldehyde, and substituting 3-bromobenzoyl chloride for 3,4-dichlorobenzoyl chloride, the title compound was prepared as a solid. MS [M+H]$^+$515.3

EXAMPLE 108

Preparation of 5-Benzofuran-2-yl-1-[1-(4-tert-butyl-phenyl)-methanoyl]-2-isobutyl-pyrrolidine-2,4-dicarboxylic Acid Following the procedure of Example 28(a)–28(d), except substituting benzofuran-2-carboxaldehyde for thiophene-2-carboxaldehyde, and substituting 4-t-butylbenzoyl chloride for 3,4-dichlorobenzoyl chloride, the title compound was prepared as a solid. MS [M+H]$^+$492.5

EXAMPLE 109

Preparation of 5-Benzofuran-2-yl-4-carbamoyl-2-isobutyl-1-[1-(4-trifluoromethyl-phenyl)-methanoyl]-pyrrolidine-2-carboxylic Acid Following the procedure of Example 28(a)–28(d), except substituting acrylamide for tert-butyl acrylate, and substituting benzofuran-2-carboxaldehyde for thiophene-2-carboxaldehyde, and substituting 4-trifluoromethylbenzoyl chloride for 3,4-dichlorobenzoyl chloride, the title compound was prepared as a solid. MS [M+H]$^+$503.4

EXAMPLE 110

Preparation of 4-Carbamoyl-5-furan-2-yl-2-isobutyl-1-[1-(4-trifluoromethyl-phenyl)-methanoyl]-pyrrolidine-2-carboxylic Acid Following the procedure of Example 28(a)–28(d), except substituting acrylamide for tert-butyl acrylate, and substituting furan-2-carboxaldehyde for thiophene-2-carboxaldehyde, and substituting 4-trifluoromethylbenzoyl chloride for 3,4-dichlorobenzoyl chloride, the title compound was prepared as a solid. MS [M+H]$^+$453.4

EXAMPLE 111

Preparation of 4-Carbamoyl-2-isobutyl-5-thiazol-2-yl-1-[1-(4-trifluoromethyl-phenyl)-methanoyl]-pyrrolidine-2-carboxylic Acid Following the procedure of Example 28(a)–28(d), except substituting acrylamide for tert-butyl acrylate, and substituting thiazole-2-carboxaldehyde for thiophene-2-carboxaldehyde, and substituting 4-trifluoromethylbenzoyl chloride for 3,4-dichlorobenzoyl chloride, the title compound was prepared as a solid. MS [M+H]$^+$470.4

EXAMPLE 112

Preparation of 4-Carbamoyl-2-isobutyl-5-thiazol-2-yl-1-[1-(3-trifluoromethyl-phenyl)-methanoyl]-pyrrolidine-2-carboxylic Acid Following the procedure of Example 28(a)–28(d), except substituting acrylamide for tert-butyl acrylate, and substituting thiazole-2-carboxaldehyde for thiophene-2-carboxaldehyde, and substituting 3-trifluoromethylbenzoyl chloride for 3,4-dichlorobenzoyl chloride, the title compound was prepared as a solid. MS [M+H]$^+$470.4

EXAMPLE 113

Preparation of 4-Carbamoyl-1-[1-(3,4-dichloro-phenyl)-methanoyl]-2-isobutyl-5-thiazol-2-yl-pyrrolidine-2-carboxylic Acid Following the procedure of Example 28(a)–28(d), except substituting acrylamide for tert-butyl acrylate, and substituting thiazole-2-carboxaldehyde for thiophene-2-carboxaldehyde, the title compound was prepared as a solid. MS [M+H]$^+$471.3

EXAMPLE 114

Preparation of 1-[1-(3-Bromo-phenyl)-methanoyl]-4-carbamoyl-2-isobutyl-5-thiazol-2-yl-pyrrolidine-2-carboxylic Acid Following the procedure of Example 28(a)–28(d), except substituting acrylamide for tert-butyl acrylate, and substituting thiazole-2-carboxaldehyde for thiophene-2-carboxaldehyde, and substituting 3-bromobenzoyl chloride for 3,4-dichlorobenzoyl chloride, the title compound was prepared as a solid. MS [M+H]$^+$481.3

EXAMPLE 115

Preparation of 4-Carbamoyl-1-[1-(4-ethyl-phenyl)-methanoyl]-2-isobutyl-5-thiazol-2-yl-pyrrolidine-2-carboxylic Acid Following the procedure of Example 28(a)–28(d), except substituting acrylamide for tert-butyl acrylate, and substituting thiazole-2-carboxaldehyde for thiophene-2-carboxaldehyde, and substituting 4-ethylbenzoyl chloride for 3,4-dichlorobenzoyl chloride, the title compound was prepared as a solid. MS [M+H]$^+$430.5

EXAMPLE 116

Preparation of 1-[1-(4-tert-Butyl-phenyl)-methanoyl]-4-carbamoyl-2-isobutyl-5-thiazol-2-yl-pyrrolidine-2-carboxylic Acid Following the procedure of Example 28(a)–28(d), except substituting acrylamide for tert-butyl acrylate, and substituting thiazole-2-carboxaldehyde for thiophene-2-carboxaldehyde, and substituting 4-tert-butylbenzoyl chloride for 3,4-dichlorobenzoyl chloride, the title compound was prepared as a solid. MS [M+H]$^+$458.5

EXAMPLE 117

Preparation of 4-Carbamoyl-2-isobutyl-5-thiophen-3-yl-1-[1-(4-trifluoromethyl-phenyl)-methanoyl]-pyrrolidine-2-carboxylic Acid Following the procedure of Example 28(a)–28(d), except substituting acrylamide for tert-butyl acrylate, and substituting thiophene-3-carboxaldehyde for thiophene-2-carboxaldehyde, and substituting 4-trifluoromethylbenzoyl chloride for 3,4-dichlorobenzoyl chloride, the title compound was prepared as a solid. MS [M+H]$^+$469.4

EXAMPLE 118

Preparation of 4-Carbamoyl-5-furan-3-yl-2-isobutyl-1-[1-(4-trifluoromethyl-phenyl)-methanoyl]-pyrrolidine-2-carboxylic Acid Following the procedure of Example 28(a)–28(d), except substituting acrylamide for tert-butyl acrylate, and substituting furan-3-carboxaldehyde for thiophene-2-carboxaldehyde, and substituting 4-trifluoromethylbenzoyl chloride for 3,4-dichlorobenzoyl chloride, the title compound was prepared as a solid. MS [M+H]$^+$453.4

EXAMPLE 119

Preparation of 4-Carbamoyl-2-(1H-imidazol-4-ylmethyl)-5-thiophen-2-yl-1-[1-(4-trifluoromethyl-phenyl)-methanoyl]-pyrrolidine-2-carboxylic Acid Following the procedure of Example 28(a)–28(d), except beginning with Wang bound Fmoc-L-histidine (Trt) instead of Wang bound Fmoc-L-leucine, and substituting acrylamide for tert-butyl acrylate, and substituting 4-trifluoromethylbenzoyl chloride for 3,4-dichlorobenzoyl chloride, the title compound was prepared as a solid. MS [M+H]$^+$493.4

EXAMPLE 120

Preparation of 4-Carbamoyl-2-isobutyl-5-thiophen-2-yl-1-[1-(3-trifluoromethyl-phenyl)-methanoyl]-pyrrolidine-2-carboxylic Acid Following the procedure of Example 28(a)–28(d), except substituting acrylamide for tert-butyl acrylate, and substituting 3-trifluoromethylbenzoyl chloride for 3,4-dichlorobenzoyl chloride, the title compound was prepared as a solid. MS [M+H]$^+$469.4

EXAMPLE 121

Preparation of 4-Carbamoyl-2-isobutyl-5-thiophen-2-yl-1-[1-(3-trifluoromethyl-phenyl)-methanoyl]-pyrrolidine-2-carboxylic Acid Following the procedure of Example 28(a)–28(d), except substituting acrylamide for tert-butyl acrylate, the title compound was prepared as a solid. MS [M+H]$^+$469.4

EXAMPLE 122

Preparation of 1-[1-(3-Bromo-phenyl)-methanoyl]-4-carbamoyl-2-isobutyl-5-thiophen-2-yl-pyrrolidine-2-carboxylic Acid Following the procedure of Example 28(a)–28(d), except substituting acrylamide for tert-butyl acrylate, and substituting 3-bromomethylbenzoyl chloride for 3,4-dichlorobenzoyl chloride, the title compound was prepared as a solid. MS [M+H]$^+$480.3

EXAMPLE 123

Preparation of 4-Carbamoyl-5-furan-2-yl-2-isobutyl-1-[1-(3-trifluoromethyl-phenyl)-methanoyl]-pyrrolidine-2-carboxylic Acid Following the procedure of Example 28(a)–28(d), except substituting acrylamide for tert-butyl acrylate, and substituting furan-2-carboxaldehyde for thiophene-2-carboxaldehyde, and substituting 3-trifluoromethylbenzoyl chloride for 3,4-dichlorobenzoyl chloride, the title compound was prepared as a solid. MS [M+H]$^+$453.4

EXAMPLE 124

Preparation of 4-Carbamoyl-2-isobutyl-5-(1-methyl-1H-imidazol-2-yl)-1-(1-m-tolyl-methanoyl)-pyrrolidine-2-carboxylic Acid Following the procedure of Example 28(a)–28(d), except substituting acrylamide for tert-butyl acrylate, and substi-

EXAMPLE 125

Preparation of 4-Carbamoyl-2-isobutyl-5-(1-methyl-1H-imidazol-2-yl)-1-(1-p-tolyl-methanoyl)-pyrrolidine-2-carboxylic Acid Following the procedure of Example 28(a)–28(d), except substituting acrylamide for tert-butyl acrylate, and substituting 1-methyl-1H-imidazole-2-carboxaldehyde for thiophene-2-carboxaldehyde, and substituting m-toluoyl chloride for 3,4-dichlorobenzoyl chloride, the title compound was prepared as a solid. MS [M+H]$^+$413.4

EXAMPLE 125

Preparation of 4-Carbamoyl-2-isobutyl-5-(1-methyl-1H-imidazol-2-yl)-1-(1-p-tolyl-methanoyl)-pyrrolidine-2-carboxylic Acid Following the procedure of Example 28(a)–28(d), except substituting acrylamide for tert-butyl acrylate, and substituting 1-methyl-1H-imidazole-2-carboxaldehyde for thiophene-2-carboxaldehyde, and substituting p-toluoyl chloride for 3,4-dichlorobenzoyl chloride, the title compound was prepared as a solid. MS [M+H]$^+$413.4

EXAMPLE 126

Preparation of 4-Carbamoyl-1-[1-(4-ethyl-phenyl)-methanoyl]-2-isobutyl-5-(1-methyl-1H-imidazol-2-yl)-pyrrolidine-2-carboxylic Acid Following the procedure of Example 28(a)–28(d), except substituting acrylamide for tert-butyl acrylate, and substituting 1-methyl-1H-imidazole-2-carboxaldehyde for thiophene-2-carboxaldehyde, and substituting 4-ethylbenzoyl chloride for 3,4-dichlorobenzoyl chloride, the title compound was prepared as a solid. MS [M+H]$^+$427.5

EXAMPLE 127

Preparation of 1-[1-(4-tert-Butyl-phenyl)-methanoyl]-4-carbamoyl-2-isobutyl-5-(1-methyl-1H-imidazol-2-yl)-pyrrolidine-2-carboxylic Acid Following the procedure of Example 28(a)–28(d), except substituting acrylamide for tert-butyl acrylate, and substituting 1-methyl-1H-imidazole-2-carboxaldehyde for thiophene-2-carboxaldehyde, and substituting 4-tert-butylbenzoyl chloride for 3,4-dichlorobenzoyl chloride, the title compound was prepared as a solid. MS [M+H]$^+$455.5

EXAMPLE 128

Preparation of 4-Carbamoyl-1-[1-(3,4-difluoro-phenyl)-methanoyl]-2-isobutyl-5-(1-methyl-1H-imidazol-2-yl)-pyrrolidine-2-carboxylic Acid Following the procedure of Example 28(a)–28(d), except substituting acrylamide for tert-butyl acrylate, and substituting 1-methyl-1H-imidazole-2-carboxaldehyde for thiophene-2-carboxaldehyde, and substituting 3,4-difluorobenzoyl chloride for 3,4-dichlorobenzoyl chloride, the title compound was prepared as a solid. MS [M+H]$^+$435.4

EXAMPLE 129

Preparation of 1-[1-(Bis-trifluoromethyl-phenyl)-methanoyl]-4-carbamoyl-2-isobutyl-5-(1-methyl-1H-imidazol-2-yl)-pyrrolidine-2-carboxylic Acid Following the procedure of Example 28(a)–28(d), except substituting acrylamide for tert-butyl acrylate, and substituting 1-methyl-1H-imidazole-2-carboxaldehyde for thiophene-2-carboxaldehyde, and substituting 2,5-bistrifluoromethylbenzoyl chloride for 3,4-dichlorobenzoyl chloride, the title compound was prepared as a solid. MS [M+H]$^+$535.4

EXAMPLE 130

Preparation of 4-Carbamoyl-2-isobutyl-5-(1-methyl-1H-imidazol-2-yl)-1-(1-naphthalen-1-yl-methanoyl)-pyrrolidine-2-carboxylic Acid Following the procedure of Example 28(a)–28(d), except substituting acrylamide for tert-butyl acrylate, and substituting 1-methyl-1H-imidazole-2-carboxaldehyde for thiophene-2-carboxaldehyde, and substituting 1-naphthoyl chloride for 3,4-dichlorobenzoyl chloride, the title compound was prepared as a solid. MS [M+H]$^+$449.5

EXAMPLE 131

Preparation of 4-Carbamoyl-2-(1H-imidazol-4-ylmethyl)-5-thiophen-2-yl-1-[1-(3-trifluoromethyl-phenyl)-methanoyl]-pyrrolidine-2-carboxylic Acid Following the procedure of Example 28(a)–28(d), except beginning with Wang bound Fmoc-L-histidine (Trt) instead of Wang bound Fmoc-L-leucine, and substituting acrylamide for tert-butyl acrylate, and substituting 3-trifluoromethylbenzoyl chloride for 3,4-dichlorobenzoyl chloride, the title compound was prepared as a solid. MS [M+H]$^+$493.4

EXAMPLE 132

Preparation of 1-[1-(4-tert-Butyl-phenyl)-methanoyl]-4-carbamoyl-2-(1H-imidazol-4-ylmethyl)-5-thiophen-2-yl-pyrrolidine-2-carboxylic acid Following the procedure of Example 28(a)-28(d), except beginning with Wang bound Fmoc-L-histidine (Trt) instead of Wang bound Fmoc-L-leucine, and substituting acrylamide for tert-butyl acrylate, and substituting 4-tert-butylbenzoyl chloride for 3,4-dichlorobenzoyl chloride, the title compound was prepared as a solid. MS [M+H]$^+$ 481.5

EXAMPLE 133

Preparation of 4-Carbamoyl-2-(1H-imidazol-4-ylmethyl)-5-thiazol-2-yl-1-[1-(3-trifluoromethyl-phenyl)-methanoyl]-pyrrolidine-2-carboxylic acid Following the procedure of Example 28(a)-28(d), except beginning with Wang bound Fmoc-L-histidine (Trt) instead of Wang bound Fmoc-L-leucine, and substituting acrylamide for tert-butyl acrylate, and substituting thiazole-2-carboxaldehyde for thiophene-2-carboxaldehyde, and substituting 3-trifluoromethylbenzoyl chloride for 3,4-dichlorobenzoyl chloride, the title compound was prepared as a solid. MS [M+H]$^+$ 494.4

EXAMPLE 134

Preparation of 4-Carbamoyl-2-(1H-imidazol-4-ylmethyl)-5-thiazol-2-yl-1-[1-(4-trifluoromethyl-phenyl)-methanoyl]-pyrrolidine-2-carboxylic acid Following the procedure of Example 28(a)-28(d), except beginning with Wang bound Fmoc-L-histidine (Trt) instead of Wang bound Fmoc-L-leucine, and substituting acrylamide for tert-butyl acrylate, and substituting thiazole-2-carboxaldehyde for thiophene-2-carboxaldehyde, and substituting 4-trifluoromethylbenzoyl chloride for 3,4-dichlorobenzoyl chloride, the title compound was prepared as a solid. MS [M+H]$^+$ 494.4

Also included in the present invention is a alternative process according to Scheme 3 for the synthesis of compounds of Example 15 and of the compounds of Examples 135–147:

Scheme 3

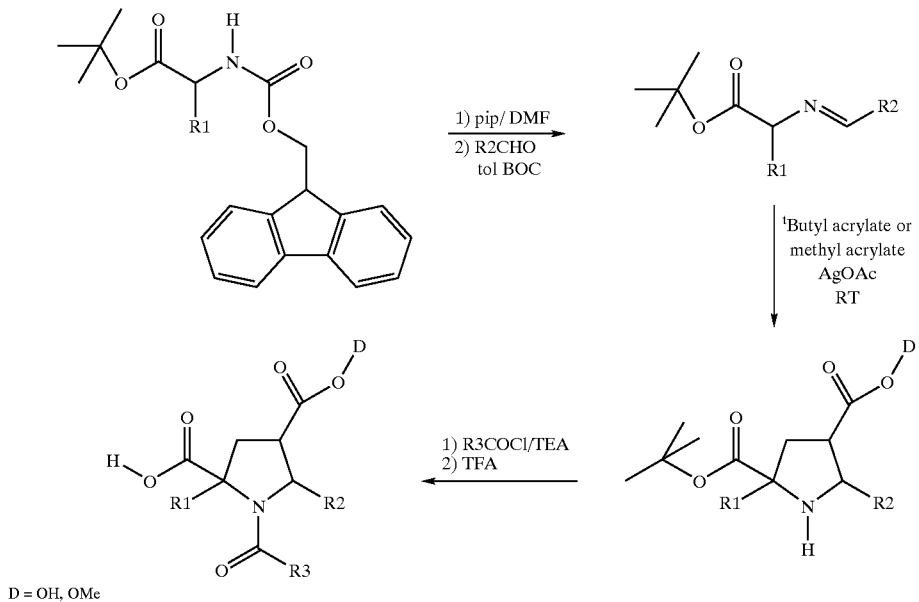

D = OH, OMe

EXAMPLE 15

Alternative Preparation According to Scheme 3

Preparation of 1-[1-(4-trifluoromethyl-phenyl)-methanoyl]-2-isobutyl-5-thiophen-2-yl-pyrrolidine-2,4-dicarboxylic acid a) 4-Methyl-2-[(thiophen-2-ylmethylene)-amino]-pentanoic acid-t-butyl ester To a stirred solution of leucine t-butyl ester (10 g) in toluene (100 mL) is added thiophene-2-carboxaldehyde (5.0 mL) and the mixture is heated to 90° C. for 2 hours. The mixture was cooled, washed with water, dried over magnesium sulfate, filtered, and evaporated to an oil (14.5 g).

b) 2-Isobutyl-5-thiophen-2-yl-pyrrolidine-2,4-dicarboxylic acid 2,4-di-tert-butyl ester The compound 135(a) was dissolved in acetonitrile (300 mL) and stirred at room temperature. Tert-butyl acrylate (2 eq., 15 mL) was added, followed by silver acetate (1.5 eq., 12.92 gm) and triethylamine (1.0 eq, 7.2 mL). The mixture was stirred for 16 hours, then poured into 250 mL of saturated ammonium chloride. The mixture was extracted three times with diethyl ether. The organic extracts were combined, washed with water, dried over magnesium sulfate, filtered, and evaporated to an oil.

c) 1-[1-(4-trifluoromethyl-phenyl)-methanoyl]-2-isobutyl-5-thiophen-2-yl-pyrrolidine-2,4-dicarboxylic acid 2,4-di-tert-butyl ester A portion of compound 135(b) (0.55 gm) was dissolved in tetrahydrofuran (2.5 mL) and treated with triethylamine (1.1 eq., 0.2 mL) and 4-trifluoromethylbenzoyl chloride (1.1 eq., 0.2 mL). The mixture was allowed to stir for 14 hours. The mixture was diluted with dichloromethane (10 mL) and washed with water. The organic layer was dried over magnesium sulfate, filtered, and evaporated to give a solid. The crude solid was purified by preparative HPLC to give the title compound as a white solid.

d) 1-[1-(4-trifluoromethyl-phenyl)-methanoyl]-2-isobutyl-5-thiophen-2-yl-pyrrolidine-2,4-dicarboxylic acid Compound 135c was stirred in neat trifluoroacetic acid for 1 hour, diluted with dichloroethane and evaporated to give a tan solid which was chromatographed using Gilson reverse phase HPLC to give the desired compound as a solid. MS [M+H]$^+$ 470:1

EXAMPLE 135

Preparation of 1-[1-(4-cyano-phenyl)-methanoyl]-2-isobutyl-5-thiophen-2-yl-pyrrolidine-2,4-dicarboxylic acid Following the procedure of Scheme 3 except substituting 4-cyanobenzoyl chloride for 4-trifluoromethyl-benzoyl chloride, the title compound was prepared as a solid. MS [M+H]$^+$ 427.1

EXAMPLE 136

Preparation of 1-[1-(4-nitro-phenyl)-methanoyl]-2-isobutyl-5-thiophen-2-yl-pyrrolidine-2,4-dicarboxylic acid Following the procedure of Scheme 3 except substituting 4-nitrobenzoyl chloride for 4-trifluoromethyl-benzoyl chloride, the title compound was prepared as a solid. MS [M+H]$^+$ 447.0

EXAMPLE 137

Preparation of 2-Isobutyl-5-thiophen-2-yl-1-(1-thiophen-2-yl-methanoyl) pyrrolidine-2,4-dicarboxylic acid Following the procedure of Scheme 3 except substituting thiophene-2-carbonyl chloride for 4-trifluoromethyl-benzoyl chloride, the title compound was prepared as a solid. MS [M+H]$^+$ 408.2

EXAMPLE 138

Preparation of 5-sec-Butyl-2-isobutyl-1-[1-(4-trifluoromethyl-phenyl)-methanoyl]-pyrrolidine-2,4-dicarboxylic acid-4-methyl ester Following the procedure for Scheme 3 except substituting methyl acrylate for t-butyl acrylate, and substituting isobutyraldehyde for thiophene-2-carboxaldehyde, the title compound was prepared as a solid. MS [M+H]$^+$ 459.1

EXAMPLE 139

Preparation of 1-[1-(4-cyano-phenyl)-methanoyl]-2-isobutyl-5-thiophen-2-yl-pyrrolidine-2,4-dicarboxylic acid-4-methyl ester Following the procedure of Scheme 3 except substituting methyl acrylate for t-butyl acrylate, and substituting 4-cyanobenzoyl chloride for 4-trifluoromethyl-benzoyl chloride, the title compound was prepared as a solid. MS [M+H]$^+$ 441.2

EXAMPLE 140

Preparation of 1-[1-(4-nitro-phenyl)-methanoyl]-2-isobutyl-5-thiophen-2-yl-pyrrolidine-2,4-dicarboxylic acid-4-methyl ester Following the procedure of Scheme 3 except substituting methyl acrylate for t-butyl acrylate, and substituting 4-nitrobenzoyl chloride for 4-trifluoromethyl-benzoyl chloride, the title compound was prepared as a solid. MS [M+H]$^+$ 461.2

EXAMPLE 141

Preparation of 1-[1-(4-pyridyl)-methanoyl]-2-isobutyl-5-thiophen-2-yl-pyrrolidine-2,4-dicarboxylic acid-4-methyl ester Following the procedure of Scheme 3 except substituting methyl acrylate for t-butyl acrylate, and substituting 4-azabenzoyl chloride for 4-trifluoromethyl-benzoyl chloride, the title compound was prepared as a solid. MS [M+H]$^+$ 416.1

EXAMPLE 142

Preparation of 1-[1-(4-trifluoromethyl-phenyl)-methanoyl]-2-isobutyl-5-thiophen-2-yl-pyrrolidine-2,4-carboxylic acid-2-methyl ester Following the procedure of Scheme 3 except substituting leucine methyl ester for leucine-t-butyl ester, the title compound was prepared as a solid. MS [M+H]$^+$ 484.2

EXAMPLE 143

Preparation of 1-[1-(4-trifluoromethyl-phenyl)-methanoyl]-2-isobutyl-5-thiophen-2-yl-pyrrolidine-2,4-dicarboxylic acid-2-benzyl ester Following the procedure of Scheme 3 except substituting leucine benzyl ester for leucine-t-butyl ester, the title compound was prepared as a solid. MS [M+H]$^+$ 560.2

EXAMPLE 144

Preparation of 1-[1-(4-trifluoromethyl-phenyl)-methanoyl]-2-isobutyl-5-thiophen-2-yl-pyrrolidine-2,4-dicarboxylic acid 2,4 dimethyl ester Following the procedure of Scheme 3 except substituting leucine methyl ester for leucine-t-butyl ester, and substituting methyl acrylate for t-butyl acrylate, the title compound was prepared as a solid. MS [M+H]$^+$ 498.1

EXAMPLE 145

Preparation of 1-[1-(3-trifluoromethyl-phenyl)-methanoyl]-2-isobutyl-5-thiophen-2-yl-pyrrolidine-2,4-dicarboxylic acid Following the procedure of Scheme 3 except substituting 3-trifluoromethyl benzoyl chloride for 4-trifluoromethyl-benzoyl chloride, the title compound was prepared as a solid. MS [M+H]$^+$ 470.2

EXAMPLE 146

Preparation of 1-[1-(4-trifluoromethyl-phenyl)-methanoyl]-2-isobutyl-5-methyl-pyrrolidine-2,4-dicarboxylic acid Following the procedure of Scheme 3 except substituting acetaldehyde for thiophene-2-carboxaldehyde, the title compound was prepared was prepared as a solid. MS 402.4 [M+H]$^+$

EXAMPLE 147

Preparation of 1-[1-(4-trifluoromethyl-phenyl)-methanoyl]-2-isobutyl-5-(2-methylethyl)-pyrrolidine-2,4-dicarboxylic acid Following the procedure of Scheme 3 except substituting isobutyraldehyde for thiophene-2-carboxaldehyde, the title compound was prepared as a solid. MS 430.4 [M+H]$^+$ In order to use a compound of Formula (I) or a pharmaceutically acceptable salt thereof for the treatment of humans and other mammals, it is normally formulated in accordance with standard pharmaceutical practice as a pharmaceutical composition.

The present ligands can be administered by different routes including intravenous, intraperitoneal, subcutaneous, intramuscular, oral, topical, transdermal, or transmucosal administration. For systemic administration, oral administration is preferred. For oral administration, for example, the compounds can be formulated into conventional oral dosages forms such as capsules, tablets and liquid preparations such as syrups, elixirs and concentrated drops.

Alternatively, injection (parenteral administration) may be used, e.g., intramuscular, intravenous, intraperitoneal, and subcutaneous. For injection, the compounds of the invention are formulated in liquid solutions, preferably, in physiologically compatible buffers or solutions, such as saline solution, Hank's solution, or Ringer's solution. In addition, the compounds may be formulated in solid form and redissolved or suspended immediately prior to use. Lyophilized forms can also be produced.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration, for example, may be through nasal sprays, rectal suppositories, or vaginal suppositories.

For topical administration, the compounds of the invention can be formulated into ointments, salves, gels, or creams, as is generally known in the art. The amounts of various compounds to be administered can be determined by standard procedures taking into account factors such as the compound ($IC_{50}$) potency, ($EC_{50}$) efficacy, and the biological half-life (of the compound), the age, size and weight of the patient, and the disease or disorder associated with the patient. The importance of these and other factors to be considered are known to those of ordinary skill in the art.

Amounts administered also depend on the routes of administration and the degree of oral bioavailability. For example, for compounds with low oral bioavailability, relatively higher doses will have to be administered. Oral administration is a preferred method of administration of the present compounds.

Preferably the composition is in unit dosage form. For oral application, for example, a tablet, or capsule may be administered, for nasal application, a metered aerosol dose may be administered, for transdermal application, a topical formulation or patch may be administered and for transmucosal delivery, a buccal patch may be administered. In each case, dosing is such that the patient may administer a single dose.

Each dosage unit for oral administration contains suitably from 0.01 to 500 mg/Kg, and preferably from 0.1 to 50 mg/Kg, of a compound of Formula (I) or a pharmaceutically acceptable salt thereof, calculated as the free base. The daily dosage for parenteral, nasal, oral inhalation, transmucosal or transdermal routes contains suitably from 0.01 mg to 100 mg/Kg, of a compound of Formula(I). A topical formulation contains suitably 0.01 to 5.0% of a compound of Formula (I). The active ingredient may be administered from 1 to 6 times per day, preferably once, sufficient to exhibit the desired activity, as is readily apparent to one skilled in the art.

As used herein, "treatment" of a disease includes, but is not limited to prevention, retardation, prophylaxis, therapy and cure of the disease. As used herein, "diseases" treatable using the present compounds include HCV infection and/or diseases resulting from HCV infection, particularly human liver diseases, such as cirrhosis, end-stage liver disease and liver cancer.

Composition of Formula (I) and their pharmaceutically acceptable salts which are active when given orally can be formulated as syrups, tablets, capsules and lozenges. A syrup formulation will generally consist of a suspension or solution of the compound or salt in a liquid carrier for example, ethanol, peanut oil, olive oil, glycerine or water with a flavoring or coloring agent. Where the composition is in the form of a tablet, any pharmaceutical carrier routinely used for preparing solid formulations may be used. Examples of such carriers include magnesium stearate, terra alba, talc, gelatin, acacia, stearic acid, starch, lactose and sucrose. Where the composition is in the form of a capsule, any routine encapsulation is suitable, for example using the aforementioned carriers in a hard gelatin capsule shell. Were the composition is in the form of a soft gelatin shell capsule any pharmaceutical carrier routinely used for preparing dispersions or suspensions may be considered, for example aqueous gums, celluloses, silicates or oils, and are incorporated in a soft gelatin capsule shell.

Typical parenteral compositions consist of a solution or suspension of a compound or salt in a sterile aqueous or non-aqueous carrier optionally containing a parenterally acceptable oil, for example polyethylene glycol, polyvinylpyrrolidone, lecithin, arachis oil or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (I) or a pharmaceutically acceptable salt thereof which is active when administered in this way, with a binding and/or lubricating agent, for example polymeric glycols, gelatins, cocoa-butter or other low melting vegetable waxes or fats or their synthetic analogs.

Typical dermal and transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer a single dose.

No unacceptable toxological effects are expected when compounds of the present invention are administered in accordance with the present invention.

The HCV NS5B inhibitory activity of the compounds of Formula (I) was determined using standard procedures well known to those skilled in the art and described in, for example Behrens et al., EMBO J. 15:12–22 (1996) and Lohmann et al., Virology 249:108–118 (1998)

All publications, including but not limited to patents and patent applications cited in this specification are herein incorporated by reference as if each individual publication were specifically and individually indicated to be incorporated by reference as though fully set forth.

What is claimed is:

1. A compound according to formula (I)

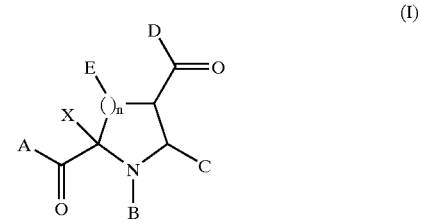

wherein:

A represents $OR_1$, $NR_1R_2$, or $R_1$ wherein $R_1$ and $R_2$ is selected from the group consisting of hydrogen, $C_{1-6}$alkyl, optionally substituted aryl, alkylaryl, arylalkyl;

B represents hydrogen, $C(O)R_1$ wherein $R_1$ is selected from the group consisting of hydrogen, $C_{1-6}$alkyl, aryl, alkylaryl, arylalkyl;

C represents hydrogen, $C_{1-6}$alkyl, or optionally substituted aryl;

D represents $OR_1$, $NR_1R_2$, or $R_1$ wherein $R_1$ and $R_2$ is selected from the group consisting of hydrogen, $C_{1-6}$alkyl, aryl, alkylaryl, arylalkyl;

E represents hydrogen, $C_{1-6}$alkyl, optionally substituted aryl, alkylaryl, arylalkyl;

X represents $C_{1-6}$alkyl, optionally substituted aryl, alkylaryl, arylalkyl;

n is 1 or 2 or 3;

or a pharmaceutically acceptable salt thereof.

2. A compound according to claim 1 selected from the group consisting of:

2-Isobutyl-5-thiophene-2-yl-1-[1-(4-trifluoromethyl-phenyl)-methanoyl]-pyrrolidine-2,4-dicarboxylic acid 4-methyl ester;

5-(3-Fluoro-phenyl)-2-isobutyl-1-[1-(4-trifluoromethyl-phenyl)-methanoyl]-pyrrolidine-2,4-dicarboxyl acid 4-methyl ester;

1-[1-(3,4-Dichloro-phenyl)-methanoyl]-5-(3-fluoro-phenyl)-2-isobutyl-pyrrolidine-2,4-dicarboxylic acid 4-methyl ester;

2-Isobutyl-5-(3-methoxy-phenyl)-1-[1-(4-trifluoromethyl-phenyl)-methanoyl]-pyrrolidine-2,4-dicarboxylic acid 4-methyl ester;
1-[1-(3,4-Dichloro-phenyl)-methanoyl]-2-isobutyl-5-(3-methoxy-phenyl)-pyrrolidine-2,4-dicarboxylic acid 4-methyl ester;
5-(2-Chloro-5-trifluoromethyl-phenyl)-2-isobutyl-1-[1-(4-trifluoromethyl-phenyl)-methanoyl]-pyrrolidine-2,4-dicarboxylic acid 4-methyl ester;
5-(2-Chloro-5-trifluoromethyl-phenyl)-1-[1-(3,4-dichloro-phenyl)-methanoyl]-2-isobutyl-pyrrolidine-2,4-dicarboxylic acid 4-methyl ester;
2-Benzyl-5-(2-chloro-5-trifluoromethyl-phenyl)-1-[1-(4-trifluoromethyl-phenyl)-methanoyl]-pyrrolidine-2,4-dicarboxylic acid 4-methyl ester;
2-Benzyl-5-thiophen-2-yl-1-[1-(4-trifluoromethyl-phenyl)-methanoyl]-pyrrolidine-2,4-dicarboxylic acid 4-methyl ester;
2-Benzyl-1-[1-(3,4-dichloro-phenyl)-methanoyl]-5-thiophen-2-yl-pyrrolidine-2,4-dicarboxylic acid 4-methyl ester;
2-Benzyl-5-(3-fluoro-phenyl)-1-[1-(4-trifluoromethyl-phenyl)-methanoyl]-pyrrolidine-2,4-dicarboxylic acid 4-methyl ester;
2-Benzyl-1-[1-(3,4-dichloro-phenyl)-methanoyl]-5-(3-fluoro-phenyl)-pyrrolidine-2,4-dicarboxylic acid 4-methyl ester;
2-Benzyl-5-(3-methoxy-phenyl)-1-[1-(4-trifluoromethyl-phenyl)-methanoyl]-pyrrolidine-2,4-dicarboxylic acid 4-methyl ester;
5-(3-Bromo-4,5-dimethoxy-phenyl)-2-methyl-1-[1-(4-trifluoromethyl-phenyl)-methanoyl]-pyrrolidine-2,4 dicarboxylic acid 4-methyl ester;
2-Isobutyl-5-thiophene-2-yl-1-[1-(4-trifluoromethyl-phenyl)-methanoyl]-pyrrolidine-2,4-dicarboxylic acid;
1-[1-(3,4-Dichloro-phenyl)-methanoyl]-5-(3-fluoro-phenyl)-2-isobutyl-pyrrolidine-2,4-dicarboxylic acid;
1-[1-(3,4-Dichloro-phenyl)-methanoyl]-2-isobutyl-5-(3-methoxy-phenyl)-pyrrolidine-2,4-dicarboxylic acid;
5-(2-Chloro-5-trifluoromethyl-phenyl)-1-[1-(3,4-dichloro-phenyl)-methanoyl]-2-isobutyl-pyrrolidine-2,4-dicarboxylic acid;
5-(2-Chloro-5-trifluoromethyl-phenyl)-2-isobutyl-1-[1-(4-trifluoromethyl-phenyl)-methanoyl]-pyrrolidine-2,4-dicarboxylic acid;
1-[1-(3,4-Dichloro-phenyl)-methanoyl]-2-isobutyl-5-(2,3,5-trichloro-phenyl)-pyrrolidine-2,4-dicarboxylic acid;
5-(3-Bromo-4,5-dimethoxy-phenyl)-2-methyl-1-[1-(4-trifluoromethyl-phenyl)-methanoyl]-pyrrolidine-2,4 dicarboxylic acid;
2-Benzyl-5-thiophen-2-yl-1-[1-(4-trifluoromethyl-phenyl)-methanoyl]-pyrrolidine-2,4-dicarboxylic acid;
2-Benzyl-1-[1-(3,4-dichloro-phenyl)-methanoyl]-5-(3-fluoro-phenyl)-pyrrolidine-2,4-dicarboxylic acid;
2-Benzyl-5-(3-fluoro-phenyl)-1-[1-(4-trifluoromethyl-phenyl)-methanoyl]-pyrrolidine-2,4-dicarboxylic acid;
2-Benzyl-5-(3-methoxy-phenyl)-1-[1-(4-trifluoromethyl-phenyl)-methanoyl]-pyrrolidine-2,4-dicarboxylic acid;
2-Benzyl-5-(2-chloro-5-trifluoromethyl-phenyl)-1-[1-(4-trifluoromethyl-phenyl)-methanoyl]-pyrrolidine-2,4-dicarboxylic acid; and
2-Benzyl-1-[1-(3,4-dichloro-phenyl)-methanoyl]-5-(2,3,5-trichloro-phenyl)-pyrrolidine-2,4-dicarboxylic acid;
or a pharmaceutically acceptable salt thereof.

3. A method of treating or preventing infection which comprises administering to a subject in need thereof, an effective amount of a compound according to claim 1.

4. A method according to claim 3 which involves inhibiting HCV.

5. A method according to claim 3 in which the compound is administered in an oral dosage form.

6. A method for the preparation of the compound according to claim 1, having the formula:

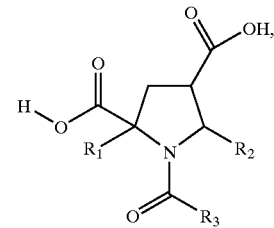

wherein:
$R_1$ is $C_{1-6}$alkyl, optionally substituted aryl, alkylaryl, arylalkyl,
$R_2$ is hydrogen, $C_{1-6}$alkyl, or optionally substituted aryl, and
$R_3$ is selected from the group consisting of hydrogen, $C_{1-6}$alkyl, aryl, alkylaryl, arylalkyl, said method comprising the steps of:
1) treating a Wang bound Fmoc-L-leucine derivative having the formula:

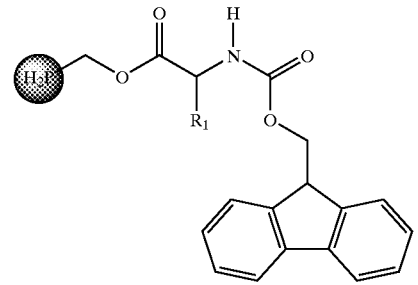

with an aldehyde, $R_2$-CHO, to form a compound having the formula:

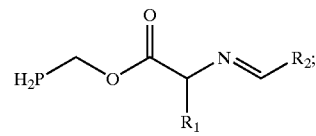

2) converting the compound formed in step 1) to a compound having the formula:

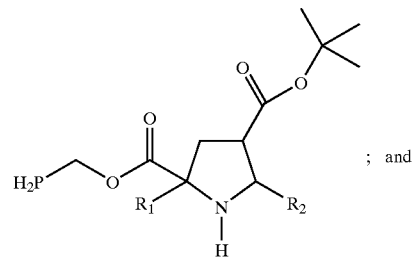

3) treating the compound formed in step 2) with $R_3$COCl, followed by treatment with an acid, to form said compound.

7. A method for the preparation of the compound according to claim 1, having the formula:

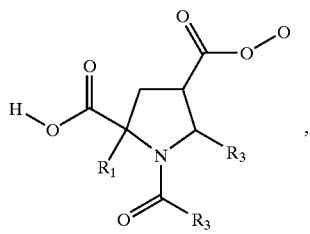

wherein:
D is OH or NH$_2$,
R$_1$ is C$_{1-6}$alkyl, optionally substituted aryl, alkylaryl, arylalkyl,
R$_2$ is hydrogen, C$_{1-6}$alkyl, or optionally substituted aryl, and
R$_3$ is selected from the group consisting of hydrogen, C$_{1-6}$alkyl, aryl, alkylaryl, arylalkyl, said method comprising the steps of:
1) treating a Wang bound Fmoc-L-leucine derivative having the formula:

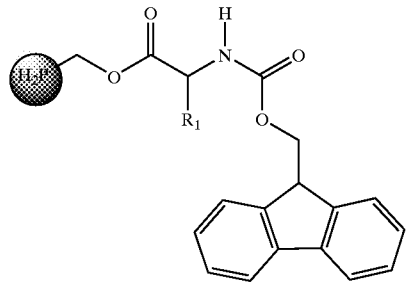

with an aldehyde, R$_2$-CHO, to form a compound having the formula:

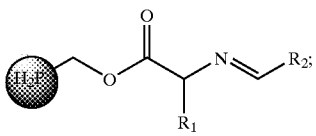

2) converting the compound formed in step 1) to a compound having the formula:

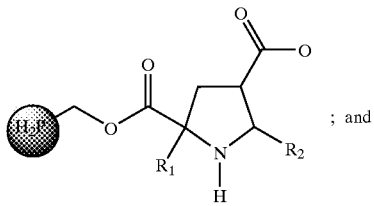

; and 3) treating the compound formed in step 2) with R$_3$COCl, followed by treatment with an acid, to form said compound.

8. A method for the preparation of the compound according to claim 1, having the formula:

wherein:
D is OH or OMe,
R$_1$ is C$_{1-6}$alkyl, optionally substituted aryl, alkylaryl, arylalkyl,
R$_2$ is hydrogen, C$_{1-6}$alkyl, or optionally substituted aryl, and
R$_3$ is selected from the group consisting of hydrogen, C$_{1-6}$alkyl, aryl, alkylaryl, arylalkyl, said method comprising the steps of:
1) treating a compound having the formula:

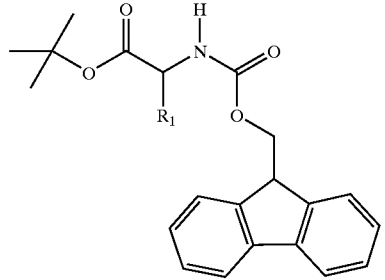

with an aldehyde, having the formula R$_2$-CHO, to form a compound having the formula:

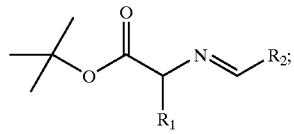

2) converting the compound formed in step 1) to a compound having the formula:

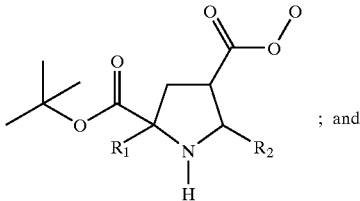

; and 3) treating the compound formed in step 2) with R$_3$COCl, followed by treatment with an acid, to form said compound.

* * * * *